US005756802A

United States Patent [19]
Li et al.

[11] Patent Number: 5,756,802
[45] Date of Patent: May 26, 1998

[54] AMMOXIDATION PROCESS FOR PRODUCING ACETONITRILE

[75] Inventors: Yuejin Li, Wescosville; John Nelson Armor, Crefield; Peter Charles Hohl, Easton, all of Pa.

[73] Assignee: Air Products and Chemicals, Inc., Allentown, Pa.

[21] Appl. No.: 756,290

[22] Filed: Nov. 25, 1996

Related U.S. Application Data

[63] Continuation-in-part of Ser. No. 526,299, Sep. 11, 1995, abandoned.

[51] Int. Cl.⁶ ............................................. C07C 253/24
[52] U.S. Cl. .................................... 558/319; 558/315
[58] Field of Search ................................ 558/315, 435, 558/319

[56] References Cited

U.S. PATENT DOCUMENTS

| | | | |
|---|---|---|---|
| 3,321,507 | 5/1967 | Ginnasi et al. | 260/465.3 |
| 3,925,447 | 12/1975 | Gelbein | 260/465 |
| 4,192,776 | 3/1980 | Grasselli et al. | 252/432 |
| 4,736,054 | 4/1988 | Attig et al. | 558/319 |

FOREIGN PATENT DOCUMENTS 738657 6/1980 U.S.S.R. .

OTHER PUBLICATIONS

Dixon and Burgoyne, "Nitriles from Olefins and Ammonia Via One–Carbon Homologation", *Applied Catalysis*, 20, pp. 79–90 (1986).

Cantani and Centi, "Selective Ethane Ammoxidation to Acetonitrile on Alumina–supported Niobium–Antimony Oxides", *J. Chem. Soc., Chem. Commun.*, pp. 1081–1083 (1991).

Centi et al. "Propane Ammoxidation to Acrylonitrile—An Overview", *Catalysis Today*, 13, pp. 661–666 (1992).

Mizuno et al., "Direct Amination of Lower alkenes with Ammonia over Zeolite Catalysts", *Studies in Surface Science & Catalysis*, 90, pp. 71–76 (1995).

Miyamoto et al., "Selective Ammoxidation of Propane on Vanaddoaluminophosphate Catalysts", *Zeolites: Facts, Figures, Future*, pp. 1233–1241 (1989).

Takahashi et al., "Acetonitrile Formation from Ethylene and Ammonia over $Zn^{2+}$ and $Cd^{2+}$ Exchanged Y–zeolites", *Chemistry Letters*, pp. 1323–1324 (1994).

*Primary Examiner*—Johann Richter
*Assistant Examiner*—Ebenezer Sackey
*Attorney, Agent, or Firm*—Keith D. Gourley

[57] ABSTRACT

Acetonitrile is produced directly from alkanes or alkenes by ammoxidation over a catalyst which is a silica–alumina exchanged with a metal of Period 4, Groups VIIA and VIII of the Periodic Table. The silica–alumina can be amorphous but is preferably crystalline zeolite. Preferred zeolite include ZSM-5, beta, NU-87 and USY. Cobalt is the favored metal for exchange. Particularly good results are obtained when the zeolite has been modified with a surface coating of silicon oxides prior to the metal exchange or modified with a boron or phosphorous containing compound followed by calcination. Ammoxidation of alkanes produce alkenes as a byproduct which can be recycled to the reaction to increase acetonitrile yield.

24 Claims, No Drawings

5,756,802

1

AMMOXIDATION PROCESS FOR PRODUCING ACETONITRILE

CROSS-REFERENCE TO RELATED APPLICATIONS

This application is a continuation-in-part to copending U.S. patent application Ser. No: 08/526,299, filed Sep. 11, 1995 now abandoned, the specification and claims which are incorporated by reference and made a part of this application.

STATEMENT REGARDING FEDERALLY SPONSORED RESEARCH OR DEVELOPMENT

Not applicable.

TECHNICAL FIELD OF THE INVENTION

This invention relates to an ammoxidation process for catalytically converting a feedstock comprising a source of hydrocarbon, ammonia and oxygen to acetonitrile. The invention also relates to a class of zeolites prepared by metal exchange which selectively produce acetonitrile, a saturated nitrile, instead of acrylonitrile, an unsaturated nitrile.

BACKGROUND OF THE INVENTION

Industry has been searching for an efficient method of synthesizing saturated nitriles directly from hydrocarbons such as alkanes and alkenes which are readily available and relatively inexpensive. Saturated nitriles, such as acetonitrile, are used as chemical intermediates in the synthesis of flavone and flavonol pigments. Dixon and Burgoyne, "Nitriles from Olefins and Ammonia Via One-Carbon Homologation", *Applied Catalysis*, 20, pp 79–90 (1986) present a review of patent and open literature on this subject and describe reactions of ethylene with ammonia using cobalt (Co) on alumina, and reduced nickel oxide on alumina to obtain propionitrile. Further work with ethylene, propylene and isobutylene feedstocks using a reduced NiO supported catalyst produced nitriles of the next higher homologue.

Ammoxidation of ethane to produce acetonitrile using a Cr—Mo oxide based catalyst is described in USSR patent SU-738657, Aliev et al. (1980). The highest yield obtained was 10 percent using a Cr—Nb—Mo oxide catalyst at 400° C. and a 19 second contact time. A decade later, Catani and Centi, "Selective Ethane Ammoxidation to Acetonitrile on Alumina-supported Niobium-Antimony Oxides", *J. Chem. Soc., Chem. Commun.*, pp 1081–3 (1991) pointed out that considerable academic and industrial effort was being directed toward developing new processes based on alkane feedstocks. The investigators describe converting ethane or propane to acetonitrile in the presence of ammonia and oxygen using a catalyst based on Nb—Sb mixed oxides supported on alumina. Acetonitrile is said to be useful as a solvent and as a chemical intermediate.

Centi et al. "Propane Ammoxidation to Acrylonitrile—An Overview", *Catalysis Today*, 13, pp 661–6 (1992) report acrylonitrile formation by ammoxidation of propane using V-Al-antimonate catalyst systems. In a review of other catalysts for this reaction, vanadyl pyrophosphate was mentioned for propane ammoxidation but the investigators stated that the results were not very promising. V-silicalite and V-aluminophosphate catalysts also gave low selectivities to the desired products. Cited patent literature refer mainly to two catalyst systems for this reaction, V-antimonate and Bi-V-molybdate.

2

Although zeolite catalysts have become quite popular in other reactions, they have not shown particular promise in nitrile synthesis. Mizuno et al., "Direct Amination of Lower Alkenes with Ammonia over Zeolite Catalysts", *Studies in Surface Science & Catalysis*, 90, pp 71–6 (1995) Elsevier, Amsterdam, review reactions catalyzed with zeolites, namely catalytic cracking and residual hydrocracking, hydration and ketonization of lower alkenes, synthesis of dimethylamine from methanol and ammonia, and direct amination of 2-methylpropene. The authors report on a study of amination of ethene and 2-methylpropene over zeolite catalysts such as ZSM-5, ferrierite, L-type, offretite/erionite, mordenite and Y. Products were t-butylamine from 2-methylpropene and ethylamine from ethene. The results are limited to addition reactions of ammonia with alkenes to form amines which are performed in the absence of oxygen.

Miyamoto et al., "Selective Ammoxidation of Propane on Vanadoaluminophosphate Catalysts", *Zeolites: Facts, Figures, Future*, pp 1233–41 (1989) Elsevier, Amsterdam, teach that vanadium oxide catalysts are industrially important for a number of processes including ammoxidation of hydrocarbons. The investigators also describe preparing a vanadium silicate by replacing aluminum (Al) in ZSM-5 zeolite at the gel formation stage which incorporates vanadium (V) into the silicate structure and provides a structure which differs from V-exchanged zeolite. Because aluminophosphates (AlPO) have shown catalytic activity, the authors investigated aluminophosphate crystals having incorporated vanadium ions (VAPO) and compared the catalytic activity of such catalysts to the V-silicates. Acrylonitrile, acetonitrile, CO and $CO_2$ were obtained as products. The reference states that the V-silicate was not very effective for the ammoxidation of propene to an unsaturated nitrile such as acrylonitrile.

Takahashi et al., "Acetonitrile Formation from Ethylene and Ammonia over $Zn^{2+}$ and $Cd^{2+}$ Exchanged Y-zeolites", *Chemistry Letters*, pp 1323–24 (1994) present a review of catalytic formation of nitriles from alkenes and ammonia in the absence of oxygen. Catalysts included are Co, Mo oxide, alumina and nickel. The authors' work was focused on $Cd^{2+}$ and $Zn^{2+}$ exchanged Y zeolites which provided higher activity than alumina. The reaction feed was ethylene, ammonia and helium, and the reaction product was acetonitrile. The NaY-zeolite was reported to have no activity for acetonitrile formation and HY-zeolite was minimally active. The best activity reported was $1.43 \times 10^{-6}$ mol per min. per gram of product using the $Zn^{2+}$ exchanged catalyst. Even this result is too low to have industrial significance.

U.S. Pat. No. 4,736,054 teaches a process for converting n-butane to acrylonitrile and hydrogen cyanide wherein a gaseous mixture of n-butane, ammonia and oxygen is reacted in the presence of a metal promoted highly siliceous zeolite comprising ZSM-5, ZSM-5 type aluminosilicate zeolites, or aluminum-free ZSM-5 type zeolites. According to the Summary of the Invention, the catalyst is a metal promoted highly siliceous zeolite represented by Ma(zeolite) wherein M is at lest one of a Group VIII metal, Cu, Ag, Zn, W, Mo and Cr or oxides thereof. According to the Detailed Description of the Invention, the metal component is at least one metal from Group VII, Cu, Ag, Zn, W, Mo or Cr or an oxide thereof. Example 1 teaches the ammoxidation of n-butane in the presence of ammonia and oxygen over a ZSM-5 catalyst. The conversion of n-butane was 43 percent with a product selectivity of 16 percent acrylonitrile, 3 percent HCN and 12 percent acetonitrile.

U.S. Pat. No. 3,321,507 teaches a process for producing unsaturated nitriles wherein a mixture of olefins is reacted with ammonia and oxygen in the presence of an oxidation catalyst consisting essentially of a mixture of bismuth oxide, molybdenum oxide and vanadium oxide. The vanadium content of the catalyst is between 0.5 and 3% and the reaction is conducted at a temperature between 450° and 525° C., for from 0.5 to 30 seconds. The examples state that minor amounts of acetonitrile, a saturated nitrile, are formed during the process.

U.S. Pat. No. 4,192,776 teaches a process for making acrylonitrile wherein an admixture of olefins, ammonia and oxygen are reacted in the presence of a catalyst containing a rare earth tantalum or niobium plus iron, bismuth and molybdenum and at least one element of nickel, cobalt, magnesium, zinc, cadmium or calcium.

Those skilled in the ammoxidation art recognize that it would be a distinct advance in industrial catalysis and extremely beneficial for the industry if a catalyst or a family of catalysts were available for converting light alkanes and ammonia oxidatively to saturated nitriles with a high selectivity, yield and efficiency.

BRIEF SUMMARY OF THE INVENTION

We have found that lower alkanes and alkenes can be efficiently converted to acetonitrile by ammoxidation utilizing a catalyst which is a silica-alumina, preferably a zeolite, which has been exchanged with a metal of Period 4, Groups VIIA and VIII of the Periodic Table (1968 Concise International Co. Ltd.). Alkanes or alkenes or mixtures thereof having 2 to 6 carbons, including straight chain and branched as well as cyclics, in the presence of ammonia and oxygen are contacted with the enumerated catalysts at elevated temperature. The enumerated metals provide a source of metal ions which produce active metal centers in the exchanged amorphous silica-alumina or zeolite. Preferred metal ions include $Co^{2+}$, $Ni^{2+}$, $Mn^{2+}$, $Fe^{2+}$ and $Fe^{3+}$. Among these metals, cobalt is preferred for providing the best overall results. Preferably, the base zeolite is exchanged with metal ions to yield a metal loading ranging from 1 to 10 weight percent.

Suitable Y zeolites include dealuminated Y zeolites such as USY and LZY-82 wherein a Y zeolite is treated to decrease the number of framework aluminum. For purposes of this invention, dealuminated Y zeolites are Y zeolites which have a silicon to aluminum ratio of greater than 2.5. The methods of dealumination are well known in the art, including high temperature steaming, mineral acid treatment or chemical treatment (such as with EDTA and $NH_4SiF_6$). The so-called ultra stable Y or USY is a dealuminated zeolite Y. USY is typically made by steaming $NH^{4+}$ form of Y zeolite at high temperatures followed by high temperature calcination or acid extraction.

Suitable catalysts include the above-mentioned zeolites which have been exchanged with enumerated metal ions wherein the resulting exchanged zeolite is modified by impregnation with a boron-containing compound or a phosphorous-containing compound and then calcined at a temperature ranging from 200° to 800° C. prior to conducting the process. This procedure is referred to as boron or phosphorous modification which yields a boron- or phosphorus-modified exchanged zeolite. Thus, preferred catalysts include boron-modified Beta which has been exchanged with divalent cobalt ions, boron-modified ZSM-5 which has been exchanged with divalent cobalt ions, boron-modified USY which has been exchanged with divalent cobalt ions and phosphorous-modified ZSM-5 which has been exchanged with divalent cobalt ions.

Acetonitrile is the primary product of the present invention even when $C_3$ (propane, propylene or isopropylene) and higher hydrocarbons are used in the feedstock. When using an alkane in the feedstock, one of the products is alkene which can be separated and recycled to the process or passed to an independent ammoxidation process if additional conversion of the alkene is desired. Recycle of alkene is particularly attractive because the process operates quite well using a feed mixture of alkane and alkene.

The process for producing acetonitrile comprises contacting a feedstock comprising a source of hydrocarbon which is an alkane having from 2 to 6 carbon atoms, an alkene having from 2 to 6 carbon atoms or a mixture thereof, ammonia and oxygen with a catalyst comprising a base zeolite which has been exchanged with metal ions of Period 4, Groups VIIA and VIII of the Periodic Table at a temperature ranging from 300° to 600° C., a pressure ranging from atmospheric to 10 atmospheres, and a gas hourly space velocity ranging from 1000 to 100,000 volumes of feedstock per volume of catalyst per hour to form a product mixture consisting essentially of acetonitrile and recovering the acetonitrile. A preferred source of hydrocarbon comprises a mixture of ethane and ethylene.

The process is typically conducted utilizing a feedstock wherein ammonia and the source of hydrocarbon are present in a molar ratio ranging from 0.1 to 10 and oxygen and the source of hydrocarbon are present in a molar ratio of from 0.1 to 10. Preferably, the molar ratio of ammonia to the source of hydrocarbon ranges from 0.2 to 4 and the molar ratio of the oxygen to the source of hydrocarbon ranges from 0.5 to 2. Preferred process conditions include temperatures ranging from 400° to 500° C. and space velocities ranging from 5,000 to 20,000 volumes of feedstock per volume of catalyst per hour. The product mixture typically comprises acetonitrile and alkene and the alkene is separated from the product mixture and preferably recycled into the process.

DETAILED DESCRIPTION OF THE INVENTION

This invention provides a very efficient process for synthesis of saturated nitrites such as acetonitrile directly from hydrocarbons. Suitable sources of hydrocarbons include linear and branched alkanes and alkenes having 2 to 6 carbon atoms per molecule. Suitable hydrocarbons include primary chain hydrocarbons such as ethane, ethylene, propane, propylene, n-butane, n-hexane, n-pentene and the like or branched (secondary or tertiary) chain hydrocarbons such as isobutane, isobutene, 2-methylpentene-1 and the like, or cyclic hydrocarbons such an cyclohexane, cyclohexene and the like.

The source of hydrocarbon can be a single alkane or alkene or a mixture of alkanes or alkenes, or a mixture of alkane and alkene. For convenience, these alkanes and alkenes shall be referred to as "Lower" alkanes and alkenes. Such sources of hydrocarbons are commonly available from refineries such as a mixture of ethane and ethylene or a mixture of propane and propylene. A mixture of hydrocarbons works very well in the invention since the process forms alkene in addition to acetonitrile. A favored embodiment of the invention includes the separation of such alkene product and recycle of the alkene product to the reaction feedstock to increase yield of acetonitrile.

The feedstock also includes ammonia and oxygen in amounts which, while avoiding explosive mixtures, generally fall in the range of 0.1 to 10 mols each of ammonia and oxygen per mol of hydrocarbon. Preferably the ammonia ratio to hydrocarbon is in the range of 0.5 to 4 mols per mol and the oxygen ratio to hydrocarbon is in the range of 0.5 to 2.

The catalyst is an exchanged silica-alumina which can be either amorphous or a crystalline aluminumsilicate, known generally as zeolite. Zeolites are well known catalytic materials for specific reactions and several forms are commercially available.

Although zeolites as a class have been discovered to be operative for the ammoxidation reaction, particular zeolites have been found to provide superior results in terms of conversion and selectivity to desired product. These zeolites are ZSM-5, beta, NU-87, mordenite, ZSM-11, ferrierite, Y, and chabazite. Other zeolites which can be used include, for example, Linde Type A, Linde Type L, Rho, offretite, and the like. Such zeolites are defined according to the Atlas of Zeolite Structure Types, (W. M. Meier and D. H. Olson, Butterworth-Heinemann, 4d Ed., (1996), published on behalf of the Structure Commission of the International Zeolite Association.

The catalysts are prepared by exchanging a metal salt in an aqueous solution with the desired zeolite or amorphous silica-alumina. The term, exchanged, means that the cations of the zeolite framework are replaced by metal cations by liquid or solid-state techniques without accumulating the metal salt in its neutral form within porous matrix of the zeolite. Therefore, the exchanged zeolite is exhaustively washed with deionized water to remove such neutral metal salts from the zeolite leaving only ionized metal associated with the zeolite framework.

According to liquid phase exchange techniques, the base zeolite is immersed in a large quantity of an aqueous solution containing the desired metal salt and optionally heated to elevated temperatures to accelerate the exchange of cations. Suitable metal salts include acetate, nitrate, sulfate, chloride, and the like.

According to solid state exchange techniques, the base zeolite is intimately contacted with a metal halide which corresponds with the metal to be exchanged within the zeolite framework. This mixture is heated in an inert atmosphere to an elevated temperature sufficient to cause the ion exchange to occur between the base zeolite and the metal salt. The resulting metal ion-exchanged zeolite is exhaustively washed with deionized water to remove the unexchanged metal halide. Suitable metal salts include chloride and bromide. The metals are those belonging to Period 4, Groups VIIA and VIII of the Periodic Table of the Elements (1968 Concise International Co., Ltd.). These include manganese, iron, cobalt and nickel, generally in their divalent oxidation state, although $Fe^{3+}$ is also suitable. Cobalt is the preferred metal, as shown in the results presented in the specific examples given in this specification.

The catalysts of Applicants' invention are formed by ion exchanging a zeolite wherein the metal of the metal salt exchanges with cations in the zeolite and wherein essentially no excess metal salt resides within the pores or on the surface of the zeolite.

In contrast, typical prior art zeolite catalysts are formed by impregnating a zeolite with very small amounts (a few milliliters per gram of zeolite) of a metal salt solution wherein the metal salt precipitates onto the surface or into the porous matrix of the zeolite. Typically, impregnation methods include a calcination step conducted in air wherein the metal salt is converted to its corresponding oxide and/or a reduction step conducted in hydrogen wherein the metal salt/oxide is converted to the corresponding zero valent metal. Such impregnation methods do not result in the metal of the metal salt exchanging with cations in the base zeolite. Applicants have unexpectedly discovered that acetonitrile can be selectively produced in high yield when ion exchanged zeolites are used in the process instead of the impregnated zeolites of the prior art.

Each framework $Al^{3+}$ ion in the base zeolite contributes a net negative charge to the Si—O—Al network. This negative charge needs to be balanced by cations to render its net charge neutral. The zeolites should be in forms easily exchangeable with the enumerated metals. The typical counterbalance cations in such zeolites are sodium, potassium, calcium, ammonium and hydrogen. The amount of metal cation exchanged into the amorphous silica-alumina or zeolite ranges from 10 to 100 percent of the exchange capacity of the base, which is inversely proportional to its Si/Al ratio. The loading of the metal ions in the catalyst base is generally between 0.1 and 15 weight percent. Below 0.1 percent the catalyst is minimally effective for the reaction and above 15 percent one reaches the maximum amount of metal which can reasonably be exchanged into a zeolite. Preferably the metal loading is in the range of 1 to 10 weight percent.

The catalytic activity of the exchanged catalyst is generally proportional to the amount of active metal in the zeolite. Excess amounts of metal cations above the exchange capacity of the base do not provide extra benefit to the catalyzed reaction but also do not defeat the operability of the catalyst. The procedure for exchanging metal ions in a silica-alumina base is well understood in the art and is also illustrated by examples included in this specification. Cation exchange can also be carried out via a solid-state reaction wherein a metal salt, such as $CoCl_2$, reacts at elevated temperatures with zeolitic cations such as $H^+$, $NH_4^+$ or $Na^+$. This solid-state exchange can also take place with metal oxides and zeolites at elevated temperatures. These exchange procedures are known and are reported H. G. Karge, Proceedings of 11th International Zeolite Conference, Seoul, Korea, 1996, P. PL4-1.

Although no catalyst pretreatment is required, the catalyst is typically dried at elevated temperature approximating the temperature to be used in the reaction, for example about 400 to 600 C., typically 500 C., in flowing dry gas, such as helium, nitrogen or air, before the reaction in order to stabilize the catalyst.

Exceptionally good results are obtained in the ammoxidation reaction using a catalyst which had been silicon modified to coat a layer of silicon oxides on the surface of the base zeolite. The silicon oxides are inert materials for most reactions and, by coating them on the surface of the zeolite particles, it is believed that reactions catalyzed by outer surface sites can be minimized. Improved nitrile selectivity and reduced $CO_2$ selectivity have been observed.

A convenient method of effecting this silicon modification is to suspend the $H^+$ form of the zeolite in a liquid medium, such as ethanol, and adding an organic silicon compound, such as tetraethyl orthosilicate (TEOS), to the slurry with stirring to allow the TEOS to react with the zeolite proton. Heating to about 60° to 70° C. helps insure this reaction in a reasonable time, e.g. one hour, after which the slurry can be filtered and the catalyst calcined in air to decompose the organic silicon compound to the silicon oxides. The modified base zeolite can then be exchanged with the active metal ion as described above. Silicon modification of zeolite can also be carried out in the gas phase wherein the vapor of a silicon containing organic compound is reacted with zeolitic proton at elevated temperature resulting in a grafting of the compound to the zeolite. An inert $SiO_2$ coating is created upon calcination.

The metal exchanged zeolite catalysts of the present invention can be further modified by depositing another element as a catalyst promoter such as boron or phosphorous containing compound. For example, a small amount of boric acid solution can be impregnated on a Co-ZSM-5 catalyst, which upon calcination yields boron oxide.

This catalyst modification method provides improved catalytic performance. The boron precursors can be any boron containing compound having sufficient solubility in water.

The typical amount of boron to be deposited onto the catalyst ranges from 0.1 to 5% by weight on a metal basis. Too little of boron does not render appreciable improvement and too much boron may decrease conversion of hydrocarbon probably due to physical blockage of active sites by boron. Similar catalyst improvement can be obtained by depositing a small amount of a phosphorous containing compound such as phosphate salt (e.g. ammonium hydrogen phosphate) onto the exchanged zeolites of this invention.

The Co-ZSM-5 and Co-ZSM-11 catalysts and all other zeolites of this invention of the present invention can be prepared by exchanging a metal salt with a zeolite in either an aqueous solution or in a solid-state mode. For aqueous ion exchange, the metal salts used include acetate, nitrate, sulfate, chloride or other forms of cobalt. A zeolite is a crystalline aluminum silicate material. Each framework $Al^{3+}$ ion confers a net negative charge to the Si—O—Al network which negative charge must be balanced by cations to render the material net charge natural. The zeolites used for this invention are in forms that are easily exchangeable with the enumerated metals. The typical count-balance cations are sodium, potassium, calcium, ammonium and hydrogen cations. For solid-state ion exchange, a $H^+$ form of zeolite is preferred. Cobalt halide. e.g., $CoCl_2.6H_2O$ is mixed with dry powder of a H-zeolite and heated in flowing inert gas. The resulting sample is then washed with deionized water to wash out the unexchanged cobalt chloride. The amount of metal cation exchanged in the zeolite ranges from 10 to 200% of the exchange capacity of a zeolite. The cation exchange capacity of a zeolite is inversely proportional to the Si/Al ratio of the zeolite. The catalytic activity is generally proportional to the amount of active metal in the zeolite to a point, and metal loading higher than the upper limit may not provide any extra benefit to the catalyzed reaction although they may still be effective catalysts.

The ammoxidation process is typically carried out in the gas phase by passing a stream of the feedstock (hydrocarbon, ammonia and oxygen) through the catalyst which is situated in a fixed, moving, or fluidized bed at elevated temperature, generally about 300° to 600° C., and preferably from 400° to 500° C. The pressure of the reaction can range from atmospheric pressure up to the explosive limits of the reaction mixture at the chosen temperature. Ordinarily the pressure does not exceed 10 atmospheres and stays well below that which would pose a possible hazard. There is no disadvantage in operating below atmospheric pressure if such a condition is dictated by upstream or downstream conditions.

Contact time of reactants with the catalyst is determined by the space velocity of the feedstock and gas hourly space velocities (GHSV) range from 1000 to 100.000 $h^{-1}$ (volumes of feed gas per volume of catalyst per hour). GHSV for most process conditions will not exceed 50.000 $hr^{-1}$ and the preferred space velocities are in the range of 5000 to 20.000 $hr^{-1}$.

Reaction effluent contains acetonitrile, unreacted alkane and alkene if such was included in the feed, alkene product formed from alkane present in the feed, carbon dioxide, carbon monoxide, and $N_2O$. These components can be separated by adsorption or other techniques known in the art. Unreacted hydrocarbons can be recycled to the reaction as can any alkene formed as a byproduct.

By this process light alkanes can be selectively transformed to acetonitrile and alkenes which in turn can be converted to the nitrile. Hydrogenation of the nitrile represents one approach to the synthesis of organic amines. Thus inexpensive feedstocks available from refinery streams can be directly and efficiently converted to valuable organic chemicals.

Other advantages and features of our invention will be apparent to those skilled in the art from the following examples which are illustrative only and should not be construed to unduly limit our invention.

EXPERIMENTAL SECTION

The following experiments were conducted in a microreactor system operating in a steady-state plug-flow mode at atmospheric pressure. The reactor is a U-shaped quartz tube with ¼" o.d. at the inlet section and ⅛" o.d. at the outlet section. The catalyst was situated in the outlet section at the center of an electrical furnace which surrounds the reactor tube. Quartz wool plugs were used to support and secure the catalyst bed. The reactor's gas delivery system consisted of four flow channels ($NH_3$, a hydrocarbon, e.g. $C_2H_6$, $O_2$/He mixture and He), each controlled by an independent mass flow controller, and these channels merged and mixed before going to the reactor inlet.

The concentration of $NH_3$ was varied between 2 and 20%, that of hydrocarbon between 2 and 20% and $O_2$ between 1 and 8%. The catalysts were first pelletized, crushed and sieved to 20–40 mesh before loading in the reactor. Total flow rate was controlled between 50 and 200 ml/min. The amount of catalyst varied from 0.05 to 0.4 g. The space velocity varied between 7,500 and 240,000 cc/h-g. However, a typically sample weight of 0.2 g and a flow rate of 100 cc/min were used for catalyst screening. Reaction temperature was controlled by a temperature programmer (Yokogawa, Model UP 40) and was varied between 300° to 600° C. The preferred reaction temperatures were maintained between 350° and 500° C. Although pretreatment of catalysts sample is not essential to achieve the catalytic activity, catalysts were routinely pretreated with flowing helium at 500° C. for 1 h before a reaction run in order to establish a standard operating procedure.

The reactor effluent was analyzed by two gas chromatograghs in series both equipped with a thermal conductivity detector (TCD). Hydrocarbons, nitrile, $CO_2$, and $N_2O$ were separated by a Porapak Q column, while $N_2$, $O_2$ and CO were separated by a molecular sieve 5A column. The reactor system was also connected to an on-line mass spectrometer, which confirmed the product identification. Product identifications were also conducted separately using GC-MS-IR coupling technique and by proton and $^{13}C$ NMR techniques. They all confirmed the GC identification. All routine product quantification was therefore carrier out with the GC technique.

The conversion, selectivity and yield are defined as

Conversion of ethane $X=(\Sigma_i y_i n_i)/(y_E n_E + \Sigma_i y_i n_i)$

Selectivity of product $P_i$ (carbon basis) $S_i = y_i n_i / \Sigma_i y_i n_i$

Yield of product $P_i$, $Y_i = XS_i$ where $y_i$ and $y_E$ are the mole fraction of carbon containing product $P_i$ and ethane, respectively; $n_i$ and $n_E$ are the number of carbon atoms in each molecule of product $P_i$ and ethane, respectively, and all the terms were to be evaluated for the exit stream.

Selectivity of product $P_j$ (nitrogen basis), $S_j = y_j n_j / (y_A n_A + \Sigma_j y_j n_j)$ where $y_i$ is the mole fractions of nitrogen containing product $P_j$, $n_j$ and $n_A$ are the number of nitrogen atoms in each molecule of product $P_j$ and ammonia, respectively.

EXAMPLES 1–30

Examples 1 through 30, excluding Example 25, illustrate preparation of catalyst which can be used to practice the invention. These catalysts were made by exchanging a metal salt with a zeolite or an amorphous silica-alumina in an aqueous solution. The metal salts used included acetate or nitrate forms of cobalt or nickel. The zeolite substrates used included ZSM-5, beta and mordenite in ammonium, sodium and hydrogen forms. Unless indicated otherwise, all exchanges were carried out at 70°–80° C. for 24 hours, using two identical exchanges for each catalyst. The exchanged catalyst slurry was then filtered, washed with 1 liter of deionized water, filtered again and the recovered zeolite dried overnight at 110° C. Example 25 is a comparative example which illustrates a method for impregnating a zeolite with a metal salt.

EXAMPLE 1

Synthesis of Co-Exchanged ZSM-5

Ten grams of $NH_4$-ZSM-5 (from VAW Aluminum AG, Germany) having a Si/Al atomic ratio of 12 was exchanged with 1 liter, 0.01M cobalt acetate aqueous solution. Elemental analysis showed that the Co/Al atomic ratio was 0.49, or 98 percent of the cation exchange capacity. For the divalent cation, such as $Co^{2+}$, a Co/Al atomic ratio of 0.5 is equivalent to 100 percent of its exchange capacity. The cobalt loading of this catalyst was 3.8% by weight.

EXAMPLE 2

Synthesis of Co-Exchanged ZSM-5

Thirty grams of Na-ZSM-5 (from VAW Aluminum AG, Germany) having a Si/Al atomic ratio of 12 were suspended in one liter of deionized water with stirring, and separately nine grams of cobalt acetate tetrahydrate (0.036 mol) was dissolved in another one liter of deionized water. The cobalt solution was then added to the zeolite slurry while stirring, the mixture heated to 70°–80 C. and exchanged for 24 hours. Only one exchange was performed for this preparation. After filtering the zeolite was washed with 2 liters of deionized water, filtered again and dried. By elemental analysis the obtained zeolite had the composition of 3.06 weight percent cobalt, 0.65 weight percent Na, Co/Al=0.42 (84% exchange) and Na/Al=0.23.

EXAMPLE 3

Synthesis of Co-Exchanged Modified Zeolite

This Example describes cobalt exchange with a silicon modified zeolite. A batch of $NH_4$-ZSM-5 (Si/Al=12) was calcined at 600° C. in air for 2 hours to convert the zeolite to H-ZSM-5. Twenty grams of H-ZSM-5 were suspended in 200 ml ethanol (200 proof) at room temperature. About 1.35 g of tetraethyl orthosilicate (TEOS) was injected into the slurry with stirring. This slurry was then heated to 60°–70° C. This process took about one hour. The slurry was then filtered. The obtained zeolite was calcined again at 500° C. in air for 2 hours to decompose the organic silicon compound to silicon oxides. Ten grams of this silicon modified H-ZSM-5 was then exchanged with 1 liter of 0.0275M cobalt acetate. The elemental analysis showed Co/Al=0.49 or a cobalt loading of 3.4% by weight.

EXAMPLE 4

Synthesis of Co-Exchanged Beta Zeolite

Four grams of $NH_4$-beta zeolite (obtained from The PQ Corporation, Valley Forge, Pa.) having a Si/Al ratio of 13 were exchanged with 1.4 liter, 0.005M cobalt acetate solution at 70°–80° C. for 20 hours. Elemental analysis showed Si/Al=12.9, Co/Al=0.42 for a loading of Co of 2.32% by weight.

EXAMPLE 5

Synthesis of Co-Exchanged Beta Zeolite

Twenty grams of $NH_4$-beta zeolite (obtained from The PQ Corporation) having a Si/Al ratio of 14 were exchanged once with a 2-liter, 0.02M cobalt acetate aqueous solution. Elemental analysis showed that the Co/Al atomic ratio was 0.35, or 70% of the cation exchange capacity of the zeolite. The cobalt loading of this catalyst was 2.2% by weight.

EXAMPLE 6

Synthesis of Co-Exchanged Mordenite

Ten grams of $NH_4$-mordenite (from Union Carbide) were exchanged with 1.5 liter, 0.025M cobalt acetate solution at 70°–80° C. Two exchanges were made and each lasted about 20 hours. The elemental analysis showed Si/Al=5.2, Co/Al= 0.39 for a cobalt loading of 4.8% by weight.

EXAMPLE 7

Synthesis of Ni-Exchanged ZSM-5 Zeolite

Fifteen grams of Na-ZSM-5 (Si/Al=12) were exchanged with 1 liter, 0.04M nickel nitrate solution. The elemental composition of this zeolite was Si/Al=11.0, Ni/Al=0.50 for a nickel loading of 3.92% by weight.

EXAMPLE 8

Synthesis of Co-Exchanged Amorphous Silica-Alumina

Ten grams of amorphous silica-alumina having 12% alumina by weight (obtained from W. R. Grace & Co., Davison division, Columbia, Md.) were exchanged once with 1 liter, 0.02M cobalt acetate. This catalyst had a cobalt loading of 2.98% by weight.

EXAMPLE 9

Synthesis of ZSM-11 Zeolite

ZSM-11 was synthesized according to the procedure described in U.S. Pat. No. 4,289,607. The X-ray diffraction profile of the synthesized material showed ZSM-11 structure. However, some of the materials had slight ZSM-5 character at $2\theta = \sim 45°$. The zeolite is a ZSM-11 zeolite with ZSM-5 intergrowth.

EXAMPLE 10

Co-Exchanged ZSM-11 Zeolite 5.7 g NaH-ZSM-11 was suspended in 150 ml, 1M ammonium nitrate solution and stirred at room temperature overnight. After the exchange, the ammonium form of ZSM-11 was filtered then washed with 500 ml deionized water. These procedures were repeated for another time. The resulting zeolite was then suspended in 62 ml, 0.02M cobalt acetate solution and stirred at refluxing temperature overnight. The resulting cobalt exchanged ZSM-11 was filtered, washed in 1 liter deionized water for 1 hour and then filtered again. Finally, it was dried at 110° C. overnight. The catalyst has the following elemental composition: Si/Al=30.2, Co/Al=0.39. The cobalt loading corresponds to 1.79% by weight.

EXAMPLE 11

Co-Exchanged ZSM-11 Zeolite with ZSM-5 Intergrowth 6.1 g ZSM-11/ZSM-5 intergrowth prepared according to Example 9 was suspended in 122 ml, 1M ammonium nitrate solution at room temperature with stirring overnight. After filtration, the zeolite was washed with 500 ml deionized water and filtered again. The second ammonium exchange was carried out in an oven set at 100° C. with a 100 ml, 1.2M ammonium nitrate solution. The zeolite then was filtered and washed as described above. The ammonium exchange yielded 5.37 g zeolite. Cobalt exchange of this resulting ammonium-zeolite was carried out twice with 118 ml, 0.03M cobalt acetate solution at 80° C. Each exchange lasted overnight. After the second cobalt exchange the zeolite was filtered, washed and dried at 110° C. overnight. This catalyst has the following composition: Si/Al=30, Co/Al=1.1, cobalt loading=3.2% by weight.

EXAMPLE 12

Co-Exchanged ZSM-11 Zeolite with ZSM-5 Intergrowth 15 g NaHZSM-11/ZSM-5 intergrowth was suspended in 250 ml deionized water with stirring. 2.5 g cobalt acetate tetrahydrate was dissolved in another 250 ml of deionized water. The cobalt solution was slowly added to the zeolite slurry. The slurry was heated to 70° C. and held at this temperature for 24 hours. The exchange was repeated two more times under identical conditions. After the final exchange, the Co-zeolite sample was washed with 1 liter deionized water for 1 hour. After filtration, the material was finally dried at 110° C. overnight. The catalyst has the following elemental composition: Si/Al=27.7, Co/Al=0.94, Na/Al=0.08. The cobalt loading corresponds to 3.17% by weight.

EXAMPLE 13

Preparation of Co-NU87

The Na form zeolite NU87 was synthesized according to the method of Casci et al. U.S. Pat. No. 5,102,641, 1992. The Na-NU87 zeolite was first ion exchanged with ammonium ions followed by ion exchange with cobalt ions. Five grams of Na-NU87 zeolite was suspended in a 100 ml, 1M ammonium nitrate aqueous solution at room temperature with stirring for 15 hours. The resulting zeolite was filtered and then washed with 200 ml deionized water. This process was repeated two more times. The ammonium form NU87 was then exchanged with cobalt ion in a 100 ml, 0.025M cobalt acetate aqueous solution at 80° C. for 15 h. After filtering, it was exchanged with cobalt ion for another time under identical conditions. After washing with 400 ml deionized water, the resulting Co-NU87 zeolite was dried at 110° C. overnight. This catalyst has the following elemental composition: Si/Al=1 6.9, Co/Al=0.49, with a cobalt loading corresponding to 2.85% by weight.

EXAMPLE 14

Preparation of Co-ZSM-5 Zeolite

A 40-g Na-ZSM-5 sample obtained from VAW Aluminum AG, Germany, (Si/Al=12), was suspended in 1-liter deionized water with stirring, and separately, 12 g cobalt acetate tetrahydrate (0.048 mol) was dissolved in another 1-liter batch of deionized water. The cobalt solution was added to the zeolite slurry while stirring. Then the zeolite slurry/solution was heated to 70°–80° C. and held for 24 h. After the first exchange, the zeolite was filtered out and a second exchanged was carried out as described above. After the second exchange, the resulting zeolite slurry was filtered and washed with 2 liter deionized water and filtered again. Finally, the zeolite was dried at 110° C. overnight. The obtained zeolite has following composition by elemental analysis:

Si/Al=10.8, Co/Al=0.62 and Na/Al=0.09. The cobalt loading corresponds to 4.94% by weight.

EXAMPLE 15

Boron-Modified Co-ZSM-5 Zeolite 2.45 g Co-ZSM-5 (Ex.14) was weighed out. 0.14 g boric acid ($H_3BO_3$) was dissolved in 5 ml de ionized water. The boric acid solution was added to the Co-ZSM-5 powder drop-by-drop with thorough mixing. At the end, the amount of solution added was just enough to wet the zeolite. The impregnated sample was allowed to dry in air at room temperature overnight. The sample was ground and calcined in air at 500° C. for 3 hours. The boron loading was calculated as 1% by weight on a metal basis. Different boron loadings (0.5, 0.75, 1.0, and 1.5%) were obtained by using corresponding amounts of boric acid.

EXAMPLE 16

Boron-Modified Co-ZSM-5 Zeolite 3.0 g Co-ZSM-5 (Ex.14) was weighed out. 0.091 g ammonia borane ($NH_3BH_3$, obtained from Aldrich) was dissolved in 5 ml de ionized water with heating and the solution was cooled to room temperature without precipitation. The borane solution was added to the Co-ZSM-5 powder drop-by-drop with thorough mixing. An intermittent drying at room temperature was applied in order avoid over wetting the sample. The impregnation was repeated once again. The twice impregnated sample was dried in air at room temperature overnight. The sample was ground and calcined in air at 500° C. for 3 hours. The boron loading is calculated as 1% by weight on a metal basis.

EXAMPLE 17

Preparation of Co-beta Zeolite 30 grams of $NH_4$-beta obtained from The PQ corporation (Valley Forge, Pa.) having a Si/Al ration of 12 were exchanged with a 2-liter, 0.02M cobalt acetate aqueous solution at 70°–80° C. for 24 h. The exchange was carried out twice. After the second exchange, the resulting zeolite slurry was filtered, washed with 1 liter deionized water and filtered again. Finally the zeolite was dried at 110° C. overnight. Elemental analysis showed that the Co/Al atomic ratio was 0.65. The cobalt loading of this catalyst is 4.58 % by weight.

EXAMPLE 18

Boron-Modified Co-beta Zeolite

1% of boron was impregnated on the Co-beta (Ex.17) following the identical procedure described in Example 16.

EXAMPLE 19

Co-Exchanged Ultra-Stable Y (USY)

USY represents a form of dealuminated zeolite Y, which provides an extra thermal stability. The USY used in this invention was purchased from Engelhard Co. (Iselin, N.J.) and is in $H^+$ form. The USY was first exchanged with an ammonium nitrate solution (1M, 15 ml solution/g zeolite) at room temperature to provide the $NH_{4+}$ form.

The resulting Y zeolite was then exchanged three times with a 0.05M cobalt acetate solution at 80° C., each exchange being conducted for 24 hours. The CoY sample was filtered, washed and dried. The elemental analyses show the following composition, Si/Al=2.9, Co/Al=0.55, Na/Al= 0.0. The Co loading corresponds to 9.81% by weight.

EXAMPLE 20

Boron-Modified Co-USY Zeolite

1% of boron was impregnated onto Co-USY (Ex.19) following the identical procedure described in Example 16.

EXAMPLE 21

Phosphorous-Modified Co-ZSM-5 Zeolite 3 g Co-ZSM-5 (Ex.14) was impregnated with 4 ml $(NH_4)_2HPO_4$ solution (containing 0.136 g salt) using the incipient wetness technique. This resulting material was dried at room temperature overnight and calcined in air at 500° C. for 3 h. The phosphorous loading was calculated as 1% by weight.

EXAMPLE 22

Co-Exchanged NaY Zeolite 7.5 gram $Na^+$ form of zeolite Y (LZY-52, obtained from Union Carbide Co. Moorestown, N.J.) was suspended in 600 ml de ionized water with a magnetic stirrer. A cobalt acetate solution (600 ml, 0.04M) was added to zeolite slurry with stirring. This cobalt exchange was carried out at room temperature for 24 hours. The slurry was filtered, washed with 1 liter de ionized water for 1 hour, and then filtered again. Finally, the cobalt exchanged zeolite was dried at 110° C. overnight. The catalyst had the following composition: Si/Al (atom ratio) =2.4, Co/Al=0.35, Na/Al=0.34. The Co loading corresponds to 8.84% by weight.

EXAMPLE 23

Co-Exchanged $NH_4Y$ Zeolite 10 gram $NH_4^+$ form of zeolite Y (LZY-62, obtained from Union Carbide Co. Moorestown, N.J.) was suspended in 500 ml de ionized water with a magnetic stirrer. A cobalt acetate solution (500 ml, 0.044M) was added into this zeolite slurry while stirring. This cobalt exchange was carried out twice at 70° C. for 20 hours. After the second exchange, the slurry was filtered, washed with 1 liter de ionized water for 1 hour, and then filtered again. Finally, the cobalt exchanged zeolite was dried at 110° C. overnight. The catalyst had the following composition: Si/Al (atom ratio)=2.5, Co/Al=0.49. The Co loading corresponds to 12.7% by weight.

EXAMPLE 24

Co-Exchanged Partially Dealuminated HY Zeolite

LZY-82 (obtained from Union Carbide Co. Moorestown, N.J.) was used for this catalyst preparation. LZY is a slightly dealuminated HY, having a Si/Al ratio of about 2.6. LZY-82 was first washed with 0.2M NaOH solution at 80° C. to convert it to Na form. The obtained NaY was then exchanged with 0.05M cobalt acetate solution (38 ml solution/g of zeolite). The cobalt/zeolite slurry contained about 10% excess of cobalt ion compared to the ion exchange capacity of the zeolite Y. The exchange was carried out three times at 80° C. The CoY sample was filtered, washed and dried as described in Example 23. The catalyst had the following composition: Si/Al=2.53, Co/Al= 0.58, Na/Al=0.03. The cobalt loading corresponds to 13.2% by weight.

EXAMPLE 25

Cobalt Impregnated ZSM-5

A cobalt impregnated ZSM-5 catalyst was prepared according to the procedure of Attig et al (U.S. Pat. No. 4,736,054) wherein Pt salt was replaced by a Co salt. To compare this impregnated sample against the ion exchanged Co-ZSM-5 (Ex. 1), the cobalt loading of this impregnated ZSM-5 was adjusted to the same loading as in Ex. 1 (3.8% by weight). Twenty one grams of ZSM-5 (Si/Al=12) was added to a 13.2 g, 40% silica sol solution adding enough water to yield a homogenous mixture. The material was dried at 110° C. for 1 h, then at 350° C. for 3 h. The dried material was ground and sieved to 10–35 mesh portion. A solution of 0.94 g $Co(NO_3)2.6H_2O$ in 10 cc distilled water was added to a 5 g portion of the supported ZSM-5. The resulting impregnated material was dried overnight at 110° C., then calcined to 550° C. for 4 h. A second catalyst was prepared wherein the sample was reduced with $H_2$ at 400° C. for 2h to yield a cobalt loading of 3.8% by weight.

EXAMPLE 26

Co-Exchanged Ultra-stable Y Zeolite (USY)

15 g of USY was exchanged with 1 liter, 0.1M NaOH solution at 80° C. for 3 hours. The zeolite was filtered and washed with (1 liter) de ionized water and filtered again. This resulting USY was subsequently exchanged with $NH_4^+$ then with $Co^{2+}$ according to the procedure described in Example 25. The Co-USY has the following elemental composition: Si/Al=3.0, Co/Al=0.62.

EXAMPLE 27

Co-Exchanged USY Zeolite 15 gram of USY was immersed in 300 ml, 0.37M HCl solution with stirring for 3 hours at room temperature. After the acid wash, the zeolite was washed with 1 liter of de ionized water. The resulting USY was twice exchanged with $NH_4^+$ (275 ml, 1M ammonium nitrite solution at room temperature). 10 grams of the resulting zeolite was twice exchanged with $Co^{2+}$ (1 liter, 0.036M) at 70° C, each exchange lasting 24 hours.

The resulting sample was filtered, washed and dried as in Example 22. Elemental analysis of this catalyst provided Si/Al=5.3, Co/Al=0.45. The Co loading corresponds to 6.56% by weight.

EXAMPLE 28

Co-Exchanged USY Zeolite

USY was HCl treated and washed with de ionized water as described in Example This zeolite was calcined in air at 600° C. for 3 h. The calcined zeolite was subjected to a series cation exchanges as described in Example 27. The catalyst has the following composition. Si/Al=6.9, Co/Al=0.58, Na/Al=0.00. The Co loading corresponds to 6.73% by weight.

EXAMPLE 29

Co-Exchanged USY Zeolite (Solid-State Method)

10 g USY was mixed with 3.64 g $CoCl_2 6H_2O$ in a mortar with grinding and was ball milled for 2 h. This thoroughly mixed zeolite sample was pelletized, sieved to 8–16 mesh and loaded into a treatment tube. This packed bed was flowed by a stream of He (150 cc/min) and heated up with the following temperature program. The temperature was held at 100° C. for 2 h then at 500° C. for 4 h, and the ramp rate was 2° C. /min. After the solid-state exchange, the zeolite was washed twice with 1 liter hot water (70° C.). Each wash lasted for about 0.5 h. Finally, the catalyst dried at 110° C. overnight.

EXAMPLE 30

Preparation of Co-ZSM-5

A 40-g Na-ZSM-5 sample obtained from VAW Aluminum AG, Germany, (Si/Al=12), was suspended in 1-liter deionized water with stirring, and separately, 12 g cobalt acetate tetrahydrate (0.048 mol) was dissolved in another 1-liter batch of deionized water. The cobalt solution was added to the zeolite slurry while stirring. The zeolite slurry/solution was heated to 70°–80° C. and held for 24 h. After the first exchange, the zeolite was filtered out and a second exchange was carried out as described in Example 27. After the second exchange, the resulting zeolite slurry was filtered, washed with 2 liter deionized water and filtered again. The zeolite was dried at 110° C. overnight. The zeolite has following composition by elemental analysis: Si/Al=10.8, Co/Al=0.62 and Na/Al=0.09. The cobalt loading corresponds to 4.94% by weight.

EXAMPLE 31

Table 1 presents a series of Runs wherein ethane, ammonia and oxygen are contacted with zeolites which have been exchanged with cobalt salts according to the claimed invention. A series of runs were made using a feed of 5 volume percent ethane, 10 percent ammonia, 6.5 percent oxygen and the balance helium. Total flow rate was 100 cc/min. Except for Runs 17 and 18, each Run utilized cobalt exchanged zeolites.

Run 17 used cobalt exchanged amorphous silica-alumina and Run 18 used cobalt which was impregnated onto ZSM-5 according to method described in U.S. Pat. No. 4,736,054. The catalyst charge was 0.2 g for each run. Catalyst compositions are given in Table 1 with the first number being Si/Al atomic ratio, the second number Co/Al atomic ratio, and the third cobalt loading as weight percent. Reaction temperatures are listed in Table 1 for each run. The exit stream was analyzed and Table 1 gives the conversion of ethane, selectivities for acetonitrile, ethylene and $CO_2$, and the total selectivity to acetonitrile and ethylene. Small amounts of methane and propionitrile were also present but are not included in Table 1.

TABLE 1

| Run # | Catalyst Base | Catalyst Comp. | Temp. °C. | Ethane Conv. (%) | Nitrile Sel. (%) | Ethene Sel. (%) | $CO_2$ Sel. (%) | Total $C_2$ Sel. (%) |
|---|---|---|---|---|---|---|---|---|
| 1 | ZSM-5 (Ex. 1) | 11; 0.49 3.83% | 450 | 38.2 | 48.7 | 28.5 | 20.6 | 77.2 |
| 2 | Beta (Ex. 4) | 13; 0.42 2.32% | 450 | 35.3 | 50.8 | 22.9 | 22.1 | 73.7 |
| 3 | NU-87 (Ex. 13) | 17; 0.49 2.85% | 450 | 26.7 | 46.3 | 35.6 | 14.1 | 81.9 |
| 4 | NU-87 | (same) | 500 | 36.2 | 46.3 | 39.9 | 11.5 | 86.2 |
| 5 | ZSM-11 (Ex. 10) | 30; 0.39 1.79% | 450 | 11.1 | 39.2 | 44.6 | 12.2 | 83.8 |
| 6 | ZSM-11 | (same) | 500 | 17.5 | 46.0 | 44.0 | 8.0 | 90.0 |
| 7 | Y (Ex. 24) | 2.5; 0.58 13.2% | 450 | 8.4 | 60.0 | 17.8 | 15.6 | 77.8 |
| 8 | Y | (same) | 500 | 15.8 | 44.9 | 41.4 | 12.1 | 86.3 |
| 9 | Mord. (Ex. 6) | 5.2; 0.40 4.89% | 450 | 23.6 | 27.5 | 55.0 | 15.4 | 82.5 |
| 10 | Ferr. | 8.3; 0.50 4.3% | 450 | 2.2 | 18.9 | 63.0 | 18.0 | 81.9 |
| 11 | Ferr. | (same) | 500 | 7.2 | 26.2 | 61.7 | 12.0 | 87.9 |
| 12 | Offr. | 2.8; 0.39 8.9% | 450 | 33.7 | 7.9 | 59.5 | 26.9 | 67.4 |
| 13 | Chab. | 2.3; 0.43 8.9% | 450 | 22.3 | 19.9 | 59.7 | 19.0 | 79.6 |

TABLE 1-continued

| Run # | Catalyst Base | Catalyst Comp. | Temp. °C. | Ethane Conv. (%) | Nitrile Sel. (%) | Ethene Sel. (%) | $CO_2$ Sel. (%) | Total $C_2$ Sel. (%) |
|---|---|---|---|---|---|---|---|---|
| 14 | Chab. | (same) | 500 | 43.6 | 26.4 | 49.4 | 20.1 | 75.8 |
| 15 | Linde A | 1.0; 0.31 10.2% | 400 | 1.6 | 28.6 | 14.3 | 57.1 | 42.9 |
| 16 | Linde A | (same) | 450 | 38.6 | 9.3 | 43.8 | 46.3 | 53.1 |
| 17 | $SiO_2$—$Al_2O_3$ (Ex. 8) | 4.7; 0.22 3.0% | 500 | 10.6 | 24.5 | 65.4 | 9.9 | 89.9 |
| 18 | Impreg ZSM-5 w $H_2$ reduction. (Ex. 25) | — 3.8% | 450 | 1.9 | 0.0 | 40.5 | 59.5 | 40.5 |
| 18 | Impreg ZSM-5 w/o $H_2$ reduction (Ex. 25) | — 3.8% | 450 | 4.0 | 0.0 | 32.4 | 67.6 | 32.4 |

Table 1 demonstrates that the choice of base zeolite has a significant impact on both conversion and selectivity. Runs 1, 2 and 3 using ZSM-5, beta and NU-87, respectively, provided the highest acetonitrile yield. Runs 5 and 6 using ZSM-11 had good acetonitrile selectivity but lower conversion compared to runs 1–4. This result may be due to the lower cobalt loading in the catalyst of runs 5 and 6. Run 7 using zeolite Y had a high selectivity for nitrile but substantially lower conversion compared to the Co-ZSM-5 and Co-beta catalysts. The Co-mordenite catalyst of run 9 provided a medium good conversion of ethane and selectivity for nitrile. Other zeolite catalysts, namely Co-ferrierite, runs 10 and 11, Co-chabazite, runs 13 and 14, and Co-silica-alumina, run 17, gave total $C_2$ selectivities higher than 70% which indicates promise commercially since both ethylene and acetonitrile are valuable products relative to ethane and ammonia. The catalysts based on offretite and Linde A, while operable, did not perform as well as the other zeolite-based catalysts.

Run 18 demonstrates that substantially different results are obtained when metal salts are impregnated onto a zeolite compared to exchanging such metal ions with a zeolite as required to practice the claimed invention. Run 18 demonstrates that reaction of ethane, ammonia and oxygen in the presence of cobalt impregnated ZSM-5 yields no detectable amount of acetonitrile, but provided a mixtures of products comprising carbon dioxide, ethylene, $N_2O$ and nitrogen. Thus, the impregnated zeolite catalysts presented in U.S. Pat. No. 4,736,054 function as dehydrogenation/oxidation catalysts for this subject reaction whereas Applicants' catalysts comprising metal exchanged zeolites function as ammoxidation catalysts as demonstrated in Run 1. The two samples according to Run 18 demonstrate that substantially the same results are obtained irrespective of whether the catalyst is subjected to hydrogen reduction prior to use.

EXAMPLE 32

Another series of runs was made for ethane ammoxidation using ZSM-5 zeolite exchanged with several different transition metal ions which are identified for each run in Table 2. The metal exchanged zeolites of Runs 20 through 27 were prepared using the method recited in Example 1. Selectivity and conversion data are given in Table 2 the same format as used for Table 1. Reaction conditions were the same as in Example 31.

TABLE 2

| Run # | Catalyst Base | Catalyst Comp. | Temp. °C. | Ethane Conv. (%) | Nitrile Sel. (%) | Ethene Sel. (%) | $CO_2$ Sel. (%) | Total $C_2$ Sel. (%) |
|---|---|---|---|---|---|---|---|---|
| 19 | Co (Ex. 1) | 11; 0.49 3.83% | 450 | 38.2 | 48.7 | 28.5 | 20.6 | 77.2 |
| 20 | Cu | 13.5; 0.65 4.46% | 450 | 15.0 | 0.8 | 65.6 | 33.6 | 66.4 |
| 21 | Ni | 11; 0.50 3.92% | 450 | 11.9 | 19.4 | 50.5 | 30.1 | 69.9 |
| 22 | Fe | 14.4; 0.17 1.0% | 450 | 9.2 | 16.2 | 39.3 | 42.1 | 55.5 |
| 23 | Mn | 12.7; 0.51 3.34% | 450 | 26.9 | 11.7 | 12.6 | 60.2 | 24.3 |
| 24 | Pd | 11; 0.37 4.54% | 400 | 20.3 | 1.2 | 7.5 | 91.2 | 8.7 |
| 25 | Ag | 14; 0.71 6.96% | 450 | 13.7 | 0.0 | 42.0 | 54.3 | 42.0 |
| 26 | Rh | 11.5; 0.23 2.66% | 450 | 2.0 | 0.0 | 0.0 | 100.0 | 0.0 |
| 27 | Pt | 14.2; 0.12 2.55% | 450 | 21.0 | 2.0 | 0.0 | 98.0 | 2.0 |

Table 2 demonstrates that cobalt has a distinct advantage over other metals when exchanged into ZSM-5 zeolite. Moderately good selectivities for nitrile production were obtained with Ni, Fe and Mn exchanged into ZSM-5. Cu-ZSM-5, Pd-ZSM-5 and Pt-ZSM-5 showed very low nitrile selectivity while Ag-ZSM-5 and Rh-ZSM-5 were totally inactive for nitrile production.

COMPARATIVE EXAMPLE 33

Several catalysts representing prior art metal oxide and mixed oxide catalysts typically used for propane ammoxidation or partial oxidation of alkanes were prepared or obtained to compare with the Co-ZSM-5 catalyst used in Example 31, run 1. Except as indicated in Table 3, the same feed composition, rate and reaction conditions were used for this comparison as used for Example 31. Yield of acetonitrile and rate of formation data are given in Table 3. The rate of formation of acetonitrile is expressed as mols per gram of catalyst per hour (mol/g-h). A description of the oxide catalysts used in each run is presented below:

Run 29, $V_2O_5/MgO$, 25.9 wt.% V, prepared by slurry method described by Michalakos et al., Journal of Catalysis, 140, 226–232 (1993).

Run 30, VPO, P/V atomic ratio=0.10, prepared by the above slurry method. Run 31, $MoO_3/Bi_2O_3/Al_2O_3$, 5.3% $MoO_3$, 18.1% $Bi_2O_3$, obtained from Armak Company, Pasadena, Tex.

Run 32, $SbVO_4$, Sb/V atomic ratio=1.0, prepared by slurry method described by Guttmann et al., U.S. Pat. No. 4,746,641 (1988).

33, $MoO_3$, unsupported, bulk $MoO_3$ obtained from Alpha Products, Word Hill, Mass. and pretreated with flowing ammonia (60 cc/min.). The temperature was ramped from 25° to 350° C. in 3.5 hours and held at 350° C. for one hour. The temperature was then ramped to 450° C. in 3 hours and subsequently ramped to 700° C. in 2 hours and held there for 1 hour.

Run 34, Nb/Sb oxides/$Al_2O_3$, 70 wt. % $Al_2O_3$, Nb/Sb atomic ratio=1.5, prepared by slurry method described by Catani and Centi, J. Chem. Soc., Chem. Comm., p 1081 (1991). Run 35, Cr—Zr—Mo oxides, Cr/Zr/Mo atomic ratio=18.1:1:31.2, prepared by slurry method described by Aliev et al. USSR patent SU-738657 (1980).

TABLE 3

| Run # | Catalyst Name | Catalyst Wt. (g) | Reaction Temp. °C. | Aceto- nitrile Yield (%) | Formation Rate (mol/g-h) |
|---|---|---|---|---|---|
| 28 | Co-ZSM-5 | 0.2 | 450 | 18.6 | $1.1 \times 10^{-2}$ |
| 29 | $V_2O_5$/MgO | 0.2 | 500 | 0.0 | 0.0 |
| 30 | VPO | 0.2 | 500 | 0.2 | $1.2 \times 10^{-4}$ |
| 31 | $MoO_3/Bi_2O_3/Al_2O_3$ | 0.2 | 500 | 0.6 | $3.9 \times 10^{-4}$ |
| 32 | $SbVO_4$ | 0.2 | 500 | 0.06 | $3.7 \times 10^{-5}$ |
| 33 | $MoO_3$ | 0.5 | 500 | 1.8 | $4.3 \times 10^{-4}$ |
| 34 | Nb/Sb oxides/$Al_2O_3$ | 0.5 | 500 | 1.2 | $3.0 \times 10^{-4}$ |
| 35 | Cr—Zr—Mo oxides | 0.5 | 500 | 2.6 | $6.4 \times 10^{-4}$ |

The data of Table 3 show that, compared to Co-ZSM-5, all of the oxide catalysts of runs 29–35 were quite inferior for nitrile synthesis. Their rates for acetonitrile formation at 500° C. are about two orders of magnitude below that of Co-ZSM-5 at 450° C.

EXAMPLE 34

To illustrate the effect of temperature on catalytic performance in the process of the invention, a series of ethane ammoxidation runs were made using Co-beta catalyst and temperatures ranging from 350° to 475° C. at 25° C. intervals. The catalyst composition was the same as given for run 2 of Example 31, and the feed stream and reaction conditions, except for temperature were also as for Example 31. Conversion, selectivity and yield data are given in Table 4.

TABLE 4

| Run # | Temp. °C. | Ethane Conv. (%) | Nitrile Sel. (%) | Ethylene Sel. (%) | $CO_2$ Sel. (%) | Acetonitrile Yield (%) |
|---|---|---|---|---|---|---|
| 36 | 350 | 4.2 | 63.6 | 0.0 | 33.8 | 2.7 |
| 37 | 375 | 9.8 | 75.6 | 0.0 | 21.1 | 7.4 |
| 38 | 400 | 15.8 | 67.1 | 6.7 | 22.5 | 10.7 |
| 39 | 425 | 31.5 | 61.0 | 9.0 | 20.5 | 19.2 |
| 40 | 450 | 41.3 | 59.7 | 13.0 | 19.3 | 24.7 |
| 41 | 475 | 47.4 | 55.8 | 18.2 | 18.3 | 26.4 |

The data of Table 4 show that selectivity for acetonitrile decreased only slightly increasing temperature while the ethane conversion was linearly proportional to temperature. The selectivity for $CO_2$ decreased with increasing temperature, which is the opposite of what one would expect from most oxidation reactions. The yield of acetonitrile was proportional to reaction temperature.

EXAMPLE 35

Since ammonia is an essential component of the feedstock, a series of runs were made to illustrate the effect of ammonia partial pressure in the feedstock. Ethane was ammoxidized to acetonitrile using the Co-ZSM-5 catalyst of Example 31, run 1. Reaction temperature was 400° C. and 0.1 g of catalyst was used. Otherwise, except for ammonia concentration in the feedstock, the feedstock composition and flow rate and other reaction conditions were as for Example 31. Conversion, selectivity and yield data are given in Table 5 for various ammonia levels in the feed, expressed as volume percent.

TABLE 5

| Run # | Ammonia Conc. (%) | Ethane Conv. (%) | Nitrile Sel. (%) | Ethylene Sel. (%) | $CO_2$ Sel. (%) | Aceto- nitrile Yield (%) |
|---|---|---|---|---|---|---|
| 42 | 2 | 4.5 | 39.7 | 37.9 | 16.2 | 1.8 |
| 43 | 5 | 9.2 | 46.2 | 32.7 | 15.4 | 4.2 |
| 44 | 7.5 | 14.7 | 48.0 | 31.7 | 15.3 | 7.0 |
| 45 | 10 | 19.2 | 48.4 | 33.5 | 13.7 | 9.3 |
| 46 | 15 | 22.0 | 53.4 | 35.4 | 6.5 | 11.7 |
| 47 | 20 | 23.5 | 56.3 | 34.3 | 4.7 | 13.2 |

As shown in Table 5, the partial pressure of ammonia in the feed had a significant impact on ethane conversion and product distribution. The ethane conversion and acetonitrile selectivity increased with the ammonia concentration in the feed, while the selectivity for $CO_2$ decreased with ammonia concentration. The nitrile yield was proportional to the ammonia concentration.

EXAMPLE 36

A series of runs were made using the same catalyst and conditions as given for Example 31, run 1, except the catalyst quantity was 0.1 g, the temperature was 400° C. and the ethane concentration in the feed was varied from 2 to 20 volume percent. Conversion, selectivity and yield data are given in Table 6.

TABLE 6

| Run # | Ethane Conc. (%) | Ethane Conv. (%) | Nitrile Sel. (%) | Ethylene Sel. (%) | $CO_2$ Sel. (%) | Acetonitrile Yield (%) |
|---|---|---|---|---|---|---|
| 48 | 2 | 21.0 | 47.4 | 24.3 | 26.3 | 10.0 |
| 49 | 5 | 26.8 | 41.7 | 31.6 | 23.6 | 11.1 |
| 50 | 7.5 | 22.1 | 42.9 | 35.2 | 18.4 | 9.5 |
| 51 | 10 | 19.4 | 45.1 | 36.6 | 14.3 | 8.7 |
| 52 | 15 | 15.7 | 44.4 | 40.0 | 11.1 | 7.0 |
| 53 | 20 | 13.0 | 45.3 | 41.9 | 7.9 | 5.9 |

Selectivity for acetonitrile, as shown in Table 6, was essentially independent of the partial pressure of ethane in the feed. The ethane conversion, however, after increasing as the mol percent of ethane went from 2 to 5, decreased with further increases of ethane concentration. As a result, acetonitrile yield changed in inverse proportion to ethane partial pressure.

EXAMPLE 37

To illustrate the effect of oxygen partial pressure in the feed on the ammoxidation reaction, a series of runs were made using the same catalyst and conditions used for Example 31, run 1 except that 0.1 g of catalyst was used, the temperature was 400° C., and the oxygen concentration was varied from run to run as indicated in Table 7 which also presents conversion, selectivity and yield data.

TABLE 7

| Run # | Oxygen Conc. (vol. %) | Ethane Conv. (%) | Nitrile Sel. (%) | Ethylene Sel. (%) | $CO_2$ Sel. (%) | Acetonitrile Yield (%) |
|---|---|---|---|---|---|---|
| 54 | 1.0 | 5.5 | 40.2 | 48.1 | 5.0 | 2.2 |
| 55 | 2.0 | 7.9 | 45.8 | 41.7 | 5.5 | 3.6 |
| 56 | 3.5 | 10.6 | 48.3 | 37.8 | 7.1 | 5.1 |
| 57 | 5.o | 13.7 | 49.7 | 35.3 | 9.0 | 6.8 |
| 58 | 6.5 | 17.6 | 46.3 | 35.0 | 14.1 | 8.2 |

Table 7 demonstrates that oxygen is essential for nitrile formation and that ethane conversion was proportional to the oxygen level in the feedstock. No ammoxidation to nitrile occurs in the absence of oxygen. Between 1 and 6.5 volume percent oxygen in the feed, the acetonitrile selectivity was relatively constant. The selectivity for $CO_2$ increased with oxygen concentration and the nitrile yield was proportional to oxygen level in the feed.

EXAMPLE 38

A series of runs were made to illustrate the effect of contact time, or space time, (which can also be expressed as space velocity) of the feed, on the ammoxidation reaction of the invention. In these runs, the flow rate of the feed was constant (100 cc/min.) but the amount of catalyst was varied from run to run. For run 59, active catalyst (Co-ZSM-5) was mixed with Na-ZSM-5, an inert material for this reaction, in a weight ratio of 1 to 3, and 0.2 g of this mixture (containing 0.05 g of Co-ZSM-5) was used. The reaction temperature was 375° C. and otherwise the conditions were as given for Example 31, run 1. The catalyst was Co-ZSM-5, prepared according to Example 1 and ethane was the hydrocarbon source in the feedstock. Table 8 gives the amount of catalyst and the contact time for each run as well as conversion, selectivity and yield data. Contact time or space time is defined as the ratio of catalyst weight (g) to the total feed flow rate (cc/min.) This value was multiplied by 60 to give the units used in Table 8, which are gram-seconds/cc.

TABLE 8

| Run # | Catalyst Wt. (g) | Contact Time (g-s/cc) | Ethane Conv. (%) | Nitrile Sel. (%) | Ethene Sel. (%) | $CO_2$ Sel. (%) | Acetonitrile Yield (%) |
|---|---|---|---|---|---|---|---|
| 59 | 0.05 | 0.03 | 7.7 | 45.5 | 25.3 | 30.0 | 3.5 |
| 60 | 0.10 | 0.06 | 7.8 | 58.1 | 26.2 | 10.1 | 4.5 |
| 61 | 0.20 | 0.12 | 10.0 | 60.5 | 22.2 | 12.5 | 6.1 |
| 62 | 0.40 | 0.24 | 28.3 | 49.7 | 24.8 | 23.0 | 14.0 |

Table 8 demonstrates that ethane conversion is usually proportional to the contact time. An intermediate length of contact time (run 61) appeared to provide the best acetonitrile selectivity. Within experimental limits, the longer the contact time, the higher the yield of acetonitrile.

EXAMPLE 39

Four ammoxidation runs were made using the silicon modified catalyst of Example 3 at various temperatures. For comparison, parallel runs using the unmodified form of the catalyst from Example 1 are presented in Table 9. The reaction conditions were otherwise as given in Example 31. The temperature and catalyst used for each run and the conversion, selectivity and yield data are given in Table 9.

TABLE 9

| Run # | Temp. °C. | Catalyst | Ethane Conv. (%) | Nitrile Sel. (%) | Ethene Sel. (%) | $CO_2$ Sel. (%) | Total $C_2$ Sel. (%) | Acetonitrile Yield (%) |
|---|---|---|---|---|---|---|---|---|
| 63 | 400 | Co-ZSM-5 | 29.2 | 52.2 | 26.1 | 18.8 | 78.3 | 15.2 |
| 64 | 400 | Co—(Si) ZSM-5 | 8.6 | 65.8 | 15.9 | 11.1 | 81.7 | 5.6 |
| 65 | 425 | Co-ZSM-5 | 35.8 | 52.4 | 25.6 | 19.2 | 78.0 | 18.8 |
| 66 | 425 | Co—(Si) ZSM-5 | 19.6 | 65.5 | 18.6 | 9.7 | 84.1 | 12.9 |
| 67 | 450 | Co-ZSM-5 | 38.2 | 48.7 | 28.5 | 20.6 | 77.2 | 18.6 |
| 68 | 450 | Co—(Si) ZSM-5 | 35.7 | 61.7 | 21.7 | 12.9 | 83.4 | 22.0 |

TABLE 9-continued

| Run # | Temp. °C. | Catalyst | Ethane Conv. (%) | Nitrile Sel. (%) | Ethene Sel. (%) | $CO_2$ Sel. (%) | Total $C_2$ Sel. (%) | Acetonitrile Yield (%) |
|---|---|---|---|---|---|---|---|---|
| 69 | 475 | Co-ZSM-5 | 38.4 | 42.3 | 31.6 | 22.3 | 73.9 | 16.2 |
| 70 | 475 | Co—(Si) ZSM-5 | 47.3 | 65.1 | 19.5 | 12.3 | 84.6 | 30.8 |

Table 9 demonstrates that the silicon modified form of the Co-ZSM-5 catalyst [Co—(Si)ZSM-5] produced lower ethane conversions at the lower temperatures (runs 64, 66 and 68), but gave a substantially higher conversion at 475° C. (run 70) when compared to the unmodified Co-ZSM-5 (runs 63, 65, 67 and 69). A distinct advantage for the silicon modified catalyst was its higher acetonitrile selectivity (10 percentage points higher) and the lower $CO_2$ selectivity (about one half) in comparison to the unmodified catalyst at all temperatures used in these runs. As a result the acetonitrile yield for the Co-(Si)ZSM-5 catalyst at 475° C. was about twice that of the ZSM-5 catalyst.

EXAMPLE 40

Using the same catalyst and reaction conditions as in Example 31, run 1, ammoxidation runs were carried out with ethylene as the hydrocarbon source in the feedstock instead of ethane at various temperatures. The catalyst was Co-ZSM-5 prepared as described in Example 1. The temperatures of the runs and conversion, selectivity and yield data are given in Table 10.

TABLE 10

| Run # | Temperature °C. | Ethylene Conv. (%) | Nitrile Sel. (%) | $CO_2$ Sel. (%) | Acetonitrile Yield (%) |
|---|---|---|---|---|---|
| 71 | 400 | 48.4 | 81.4 | 17.2 | 39.4 |
| 72 | 425 | 53.4 | 79.8 | 18.8 | 42.6 |
| 73 | 450 | 57.7 | 77.0 | 21.4 | 44.4 |

The data of Table 10, when compared to runs 63, 65 and 67 of Table 9, show that with the same catalyst, ethylene ammoxidation is more efficient than ethane ammoxidation in producing acetonitrile. The acetonitrile yields more than doubled where ethylene is used as the hydrocarbon source instead of ethane as the hydrocarbon source.

COMPARATIVE EXAMPLE 41

To illustrate the importance of ammonia in the feedstock for ethylene production, two runs were made with a Co-ZSM-5 catalyst as prepared in Example 1 and used in run 1 of Example 31 but with only ethane and oxygen in the feedstock. The feedstock composition was 5% by volume ethane, 6.5% oxygen and the balance helium. Flow rate was 100 cc/min. and 0.2 g of catalyst was used for both runs. Reaction temperature and conversion, selectivity and yield data are given in Table 11. For comparison, ethylene yield values are also listed in Table 11 for ammoxidation reactions under the same conditions except that 5 volume % ammonia was present in the feed.

TABLE 11

| Run # | Temp. °C. | Ethane Conv. (%) | Ethylene Sel. (%) | $CO_2$ Sel. (%) | Ethylene Yield (%) | Ethylene Yield with $NH_3$ Present (%) |
|---|---|---|---|---|---|---|
| 74 | 400 | 15.6 | 22.4 | 76.7 | 3.5 | 7.6 |
| 75 | 450 | 49.6 | 7.3 | 82.2 | 3.6 | 10.9 |

Table 11 illustrates that $CO_2$ was a major product in this reaction because ethylene produced in situ is oxidized to $CO_2$. Also, the amounts of ethylene produced were much smaller than for ethane ammoxidation using the same catalyst. It can be seen from Table 5 of Example 35 that all of the ethylene selectivities for runs 42–47 over a range of ammonia concentrations in the feed were much higher than the ethylene selectivities for runs 74 and 75 where only ethane and oxygen were the reactants.

EXAMPLE 42

Using the same conditions as in Example 31, run 1, except for temperature variations, several runs were made for the ammoxidation of propane. The feedstock consisted of 5% by volume propane, 10% ammonia, 6.5% oxygen and the balance helium. The catalysts were Co-ZSM-5 as made in Example 1 and the silicon modified form Co—(Si)ZSM-5 as made in Example 3. Conversion and selectivity data are given in Table 12 which also identifies the catalyst and temperature used for each run.

TABLE 12

| Run # | Temp. °C. | Catalyst Type | Propane Conv. (%) | Oxygen Conv. (%) | $C_2H_3N$ Sel. (%) | $CO_2$ Sel. (%) | Propene Sel. (%) | Ethene Sel. (%) | $C_3H_5N$ Sel. (%) |
|---|---|---|---|---|---|---|---|---|---|
| 76 | 375 | Co-ZSM-5 | 19 | 86 | 25 | 26 | 42 | 5 | 1 |
| 77 | 400 | Co-ZSM-5 | 26 | 97 | 28 | 28 | 35 | 6 | 2 |
| 78 | 400 | Co—(Si)ZSM-5 | 10 | 43 | 32 | 18 | 48 | 3 | 0 |
| 79 | 425 | Co-ZSM-5 | 29 | 100 | 29 | 28 | 34 | 6 | 1 |
| 80 | 425 | Co—(Si)ZSM-5 | 21 | 68 | 33 | 16 | 43 | 5 | 1 |

TABLE 12-continued

| Run # | Temp. °C. | Catalyst Type | Propane Conv. (%) | Oxygen Conv. (%) | C₂H₃N Sel. (%) | CO₂ Sel. (%) | Propene Sel. (%) | Ethene Sel. (%) | C₃H₅N Sel. (%) |
|---|---|---|---|---|---|---|---|---|---|
| 81 | 450 | Co-ZSM-5 | 31 | 100 | 29 | 30 | 31 | 7 | 1 |
| 82 | 450 | Co—(Si)ZSM-5 | 28 | 87 | 33 | 18 | 38 | 4 | 2 |
| 83 | 4775 | Co—(Si)ZSM-5 | 35 | 96 | 34 | 19 | 34 | 5 | 2 |

Table 12 demonstrates that the major products of propane ammoxidation are acetonitrile, propene and carbon dioxide. Small amounts of ethene and propionitrile are also produced. The silicon modified catalyst, Co—(Si)ZSM-5, was more selective in producing acetonitrile and less selective for $CO_2$ formation compared to the unmodified Co-ZSM-5. Further, the modified Co—(Si)ZSM-5 consumed less oxygen in the process. This means that less ammonia was being oxidized to nitrogen and less water was produced, thereby increasing the efficiency of the process. For both catalysts the formation of propionitrile was low.

EXAMPLE 43

As shown by Example 42, ammoxidation of alkanes and alkenes higher than ethane and ethylene by the process of the invention still produces primarily acetonitrile rather than the higher nitrites. This Example illustrates this result in the ammoxidation of a series of hydrocarbons over the cobalt exchanged, silicon modified ZSM-5 zeolite whose preparation is described in Example 3. Except for n-pentane ammoxidation, the feed was 5% by volume hydrocarbon, 10% ammonia, 6.5% oxygen and the balance helium. The amount of catalyst was 0.2 g, and the feed rate was 100 cc/min. In the case of n-pentane ammoxidation, the concentration was 1.2%. Table 13 provides the hydrocarbon source used for each run, the reaction temperature, and data on hydrocarbon conversion and acetonitrile selectivity, yield and rate of formation in mmol per gram of catalyst per hour.

TABLE 13

| Run # | Hydrocarbon | Temp. °C. | Hydrocarbon Conversion (%) | Nitrile Sel. (%) | Nitrile Yield (%) | Nitrile Rate (mmol/g/h) |
|---|---|---|---|---|---|---|
| 84 | ethane | 400 | 29 | 52 | 15 | 9 |
| 85 | ethane | 450 | 38 | 49 | 19 | 12 |
| 86 | propane | 400 | 26 | 28 | 7 | 4 |
| 87 | propane | 450 | 31 | 29 | 9 | 5 |
| 88 | n-butane | 400 | 29 | 75 | 22 | 14 |
| 89 | n-butane | 450 | 29 | 58 | 16 | 10 |
| 90 | iso-butane | 400 | 11 | 56 | 6 | 4 |
| 91 | iso-butane | 450 | 16 | 44 | 7 | 4 |
| 92 | iso-butylene | 400 | 3 | 55 | 2 | 1 |
| 93 | iso-butylene | 450 | 37 | 22 | 8 | 5 |
| 94 | n-pentane | 400 | 55 | 30 | 17 | 3 |

For the hydrocarbons converted, acetonitrile was the major nitrile product. Good selectivities were obtained for all the hydrocarbons, but especially for ethane, n-butane and iso-butane.

EXAMPLE 44

Comparison of Co-ZSM-11 (or Co-ZSM-11/ZSM-5 Intergrowth) and Co-ZSM-5 for Ethylene Ammoxidation Reaction with Two Feed Compositions Table 14 compares Co-ZSM-5, with two Co-ZSM-11 catalysts (Co-ZSM-11 /ZSM-5 intergrowth) for ethylene ammoxidation. Co-ZSM-11 (or Co-ZSM-11/ZSM-5 intergrowth) is significantly more selective for acetonitrile formation calculated based on $C_2$ or $NH_3$. Carbon dioxide formation is suppressed over Co-ZSM-11 (or Co-1/ZSM-5 intergrowth) compared to Co-ZSM-5. In a practical sense, this ammoxidation process may be operated in a recycle mode, where one-pass hydrocarbon conversion is less important than its selectivity. Therefore, Co-ZSM-11 (or Co-ZSM-11/ZSM-5 intergrowth) is superior to Co-ZSM-5 when ethylene is used as the hydrocarbon source in the ammoxidation process feedstock in the sense that the former is more efficient in utilizing raw material.

TABLE 14

| | Ethene Ammoxidation* at 475° C. | | | |
|---|---|---|---|---|
| | Con. C₂H₄ | Sel. based on C₂H₄ (%) | | Sel. C₂H₃N (%) |
| Run Catalyst | (%) | C₂H₃N | CO₂ | based on NH₃ |
| 95 Co-ZSM-5 (Ex. 1) | 51.0 | 64.6 | 32.8 | 29.1 |
| 96 Co-ZSM-11 (Ex. 10) | 41.1 | 80.2 | 19.2 | 41.1 |
| 97 Co-ZSM-11 (Ex. 11) | 42.9 | 79.8 | 18.5 | 39.3 |

TABLE 14-continued

| | Ethene Ammoxidation* at 475° C. | | | |
|---|---|---|---|---|
| | Con. C₂H₄ | Sel. based on C₂H₄ (%) | | Sel. C₂H₃N (%) |
| Run Catalyst | (%) | C₂H₃N | CO₂ | based on NH₃ |

*Total flow rate was 100 cc/min; 0.2 g catalyst was used; Feed composition: 5% $C_2H_4$, 10% $NH_3$, 6.5% $O_2$, balanced by He.

EXAMPLE 45

Comparison of Co-ZSM-11 (or Co-ZSM-11/ZSM-5 intergrowth) and Co-ZSM-5 for Ammoxidation of Ethylene/Ethane Mixture Table 15 demonstrates that Co-ZSM-11 (Co-ZSM-11/ZSM-5 intergrowth) is also more selective than Co-ZSM-5 for the ammoxidation of ethene/ethane (1:1) mixture. On an average, the acetonitrile selectivity (both based on $C_2$ and $NH_3$) is 10 percentage higher on Co-ZSM-11 (Co-ZSM-11/ZSM-5 intergrowth) than on Co-ZSM-5, while the $CO_2$ formation is 10 percentage lower on Co-ZSM-11 (Co-ZSM-11/ZSM-5 intergrowth).

TABLE 15

Ammoxidation[a] of Ethene/Ethane (1:1) Mixture at 475° C.

| Run | Catalyst | Conv. of $C_2$ (%) | Selectivity based on $C_2$ (%) $C_2H_3N$ | $CO_2$ | Sel. $C_2H_3N$ (%) based on $NH_3$ |
|---|---|---|---|---|---|
| 98 | Co-ZSM-5[b] (Ex.1) | 30.0 | 78.5 | 19.9 | 36.4 |
| 99 | Co-ZSM-11 (Ex. 12) | 19.5 | 90.8 | 8.2 | 47.0 |
| 100 | Co-ZSM-11 (Ex. 11) | 27.2 | 89.8 | 9.5 | 47.0 |

[a]Feed: 5% $C_2H_4$, 5% $C_2H_6$, 10% $NH_3$, and 6.5% $O_2$ balancing by He; Total flow rate was 100 cc/min; 0.2 g catalyst was used;
[b]Reaction was run at 450° C.

The current invention provides higher ammonia selectivity for the ammoxidation of ethene or the mixture of ethane and ethene by using a Co-ZSM-11 based catalyst. This invention would result in a more economical route of converting ethene or the mixture of ethane and ethene to acetonitrile or other acetonitrile based chemicals.

EXAMPLE 46

Ethane Ammoxidation Over Boron Modified Co-ZSM-5 Catalysts

Table 16 compares the catalytic performance of Co-ZSM-5 and the boron modified Co-ZSM-5 catalysts as a function of boron loading. The acetonitrile selectivity (based on $C_2$) increased from 32% for the Co-ZSM-5 catalyst to >50% for the Boron modified catalysts. Similar enhancement was found on ammonia utilization 14% vs. 24%. Interestingly, the $C_2H_6$ conversion is also increased on the B/Co-ZSM-5 catalysts with Boron loading 0.5–1.0% compared to its starting catalyst, Co-ZSM-5. In addition, Boron modification reduces $CO_2$ formation to less than half of the levels of their original catalysts.

TABLE 16

Ethane Ammoxidation[a] Over B/Co-ZSM-5 at 475° C.

| Run | Catalyst | Boron (%) | Conv. (%) $C_2H_6$ | Selectivity based on $C_2H_6$ (%) $C_2H_3N$ | $C_2H_4$ | $CO_2$ | $C_2H_3N$ Sel ($NH_3$) (%) |
|---|---|---|---|---|---|---|---|
| 101 | Co-ZSM-5 (Ex. 14) | 0 | 30.6 | 31.8 | 45.0 | 14.8 | 13.7 |
| 102 | B/Co-ZSM-5 (ex. 15) | 0.5 | 36.6 | 49.3 | 38.3 | 7.0 | 23.4 |
| 103 | B/Co-ZSM-5 (Ex. 15) | 0.75 | 35.5 | 51.3 | 37.7 | 6.1 | 23.6 |
| 104 | B/Co-ZSM-5 (Ex. 15) | 1.0 | 35.1 | 52.5 | 36.1 | 7.1 | 24.1 |
| 105 | B/Co-ZSM-5 (Ex. 15) | 1.5 | 28.7 | 52.5 | 38.2 | 5.1 | 23.1 |

[a]Feed: 10% $C_2H_6$, 10% $NH_3$, 6.5% $O_2$; 0.3 g catalyst.

EXAMPLE 47

Catalytic Performance of B/Co-ZSM-5, B/Beta and B/Co-USY

As shown in Table 17, boron modification is a general approach which can be applied to other Co-zeolite catalysts for activity enhancement. The acetonitrile selectivities over Co-beta and Co-USY are also improved by merely depositing 1% boron. However, the degree of this enhancement may vary depending on the initial selectivity/activity of a catalyst. At 475° C., the ammonia selectivity was increased by 5 and 9 percentage points on Co-beta and Co-USY, respectively. Prior to the boron modification, the ammonia selectivities on these two catalysts were already high.

The boron precursor used for this modification can be any boron containing compound with sufficient solubility in water. In addition to boric acid, ammonia borane (1% B) was used for the modification which resulted in significant enhancement on acetonitrile selectivity, 79% vs. 32% on a $C_2$ basis. On an ammonia basis, the acetonitrile selectivity increased to 23% from 14%.

TABLE 17

Effect of Boron Modification for Ethane Ammoxidation[a] at 475° C.

| Run | Catalyst | Conv. of $C_2H_6$ (%) | Selectivity based on $C_2H_6$ (%) | | | $C_2H_3N$ selec. based on $NH_3$ (%) |
|---|---|---|---|---|---|---|
| | | | $C_2H_3N$ | $C_{2H4}$ | $CO_2$ | |
| 106 | Co-ZSM-5 (Ex. 14) | 31 | 32 | 45 | 15 | 14 |
| 107 | B/Co-ZSM-5 (Ex. 15) | 35 | 53 | 36 | 7 | 24 |
| 108 | B/Co-ZSM-5 (Ex. 16) | 21 | 79 | 5 | 8 | 23 |
| 109 | Co-beta (EX. 17) | 34 | 50 | 30 | 11 | 25 |
| 110 | B/Co-beta (Ex. 18) | 34 | 58 | 25 | 8 | 30 |
| 111 | Co-USY (Ex. 19) | 17 | 53 | 27 | 14 | 29 |
| 112 | B/Co-USY (Ex. 20) | 14 | 59 | 18 | 15 | 38 |

[a]Feed composition: 10% $C_2H_6$, 10% $NH_3$, and 6.5% $O_2$ balanced by He; the total flow rate was 100 cc/min. 0.3 g catalyst was used for each run.

EXAMPLE 48

Comparison of Co-beta and B/Co-beta as a function of temperature

Co-beta and B/Co-beta are compared in Table 18 as a function of temperature. The acetonitrile selectivity over B/Co-beta is consistently higher than that over Co-beta at any given temperature on either a C2 basis or an ammonia basis.

TABLE 18

Ethane Ammoxidation[a] on Co-beta and B/Co-beta

| Run | Catalyst | T (°C.) | Conv. of $C_2H_6$ (%) | Selectivity based on $C_2H_6$ (%) | | | $C_2H_3N$ selec. based on $NH_3$ (%) |
|---|---|---|---|---|---|---|---|
| | | | | $C_2H_3N$ | $C_2H_4$ | $CO_2$ | |
| 113 | Co-beta (Ex. 17) | 425 | 26.2 | 65.5 | 14.8 | 12.6 | 22.5 |
| 114 | Co-beta (Ex. 17) | 450 | 31.7 | 57.8 | 22.3 | 11.8 | 27.8 |
| 115 | Co-beta (Ex. 17) | 475 | 34.3 | 49.9 | 29.9 | 11.1 | 24.8 |
| 116 | B/Co-beta (Ex. 18) | 425 | 20.3 | 71.4 | 10.3 | 11.6 | 34.4 |
| 117 | B/Co-beta (Ex. 18) | 450 | 27.9 | 64.9 | 18.0 | 9.2 | 32.4 |
| 118 | B/Co-beta (Ex. 18) | 475 | 33.7 | 57.6 | 25.3 | 8.5 | 30.1 |

[a]Feed composition: 10% $C_2H_6$, 10% $NH_3$, and 6.5% $O_2$ balanced by He; the total flow rate was 100 cc/min. 0.3 g catalyst was used for each run.

EXAMPLE 49

Comparison of Co-ZSM-5 and P/Co-ZSM-5 as a Function of Temperature

Table 19 illustrates the effect of phosphorous modification on a Co-ZSM-5 catalyst. Similar to boron modification, depositing 1% phosphorous onto the zeolite increases both the selectivity to acetonitrile and conversion of ethane.

TABLE 19

Phosphorous Modification of Co-ZSM-5

| Run | Catalyst | Temp (°C.) | Conv. of $C_2H_6$ (%) | Selectivity based on $C_2H_6$ (%) | | | $C_2H_3N$ selec. based on $NH_3$ (%) |
|---|---|---|---|---|---|---|---|
| | | | | $C_2H_3N$ | $C_2H_4$ | $CO_2$ | |
| 119 | Co-ZSM-5 (Ex. 14) | 450 | 30.5 | 40.0 | 42.3 | 12.0 | 17.0 |
| 120 | P/Co-ZSM-5 (Ex. 21) | 450 | 31.5 | 52.9 | 31.9 | 8.8 | 23.9 |
| 121 | Co-ZSM-5 (Ex. 14) | 475 | 30.6 | 31.8 | 45.0 | 14.9 | 13.7 |
| 122 | P/Co-ZSM-5 (Ex. 21) | 475 | 33.8 | 50.0 | 33.9 | 8.7 | 22.8 |

Feed composition: 10% $C_2H_6$, 10% $NH_3$, and 6.5% $O_2$ balanced by He; F = 100 cc/min., W = 0.3 g.

The ethane ammoxidation reaction shown in Examples 50 and 51 are run under the following conditions. 0.3 g catalyst, 20/40 mesh size, was used for the screening tests. The feed consisted of 10% $C_2H_6$, 10% $NH_3$ and 6.5% $O_2$ by volume balancing by helium. The total flow rate was 100 cc/min at ambient conditions.

EXAMPLE 50

Comparison of Co-Y Catalysts for Ethane Ammoxidation Reaction at 475° C.

As shown in Table 20, both $C_2H_3N$ selectivity (based on $C_2$ and $NH_3$) and $C_2H_6$ conversion increase as the Si/Al ratio of zeolite Y increases. The $C_2H_3N$ selectivity based on $NH_3$ is almost tripled on Co-(HCl treated) USY catalysts (Ex. 27 and 28) compared to a standard Co-Y catalyst (Ex. 22). Normally, selectivity enhancement is at the expense of activity loss. However, in this case, the $C_2H_6$ conversion is also dramatically increased (nearly double) by the dealumination treatment. Another benefit of these high Si/Al Y catalysts is much lowered $CO_2$ formation. Therefore, these dealumination treatments substantially improve catalytic performance. The solid-state preparation of Co-USY (Ex. 29) resulted in comparable catalytic performance compared to the aqueous preparation (Ex. 19). Table 20 also compares these dealuminated Y with a Co-ZSM-5 catalyst, a standard reference catalyst. The most obvious superiority of the high Si/Al Y catalysts is their much higher ammonia utilization to form $C_2H_3N$.

TABLE 20

Ethane Ammoxidation on a Series of Co-Y Catalysts at 475° C.

| Run | Catalyst | Frame work Si/Al | Bulk Si/Al | Co/Al | $C_2H_6$ conv. (%) | Sel. based on $C_2H_6$ (%) | | | $C_2H_3N$ sel. based on $NH_3$ (%) |
|---|---|---|---|---|---|---|---|---|---|
| | | | | | | $C_2H_3N$ | $C_2H_4$ | $CO_2$ | |
| 123 | Co-NaY (Ex. 22) | 2.5 | 2.5 | 0.35 | 12.2 | 27.9 | 45.7 | 18.2 | 13.4 |
| 124 | Co-Y (Ex. 23) | 2.5 | 2.5 | 0.49 | 12.7 | 36.1 | 38.7 | 20.0 | 23.9 |
| 125 | Co-Y (Ex. 24) | 3.9 | 2.6 | 0.58 | 15.3 | 45.4 | 28.4 | 21.6 | 28.4 |
| 126 | Co-USY (Ex. 19) | 9.0 | 2.9 | 0.56 | 16.8 | 52.8 | 27.4 | 14.0 | 29.3 |
| 127 | Co-USY (Ex. 26) | N/A | 3.0 | 0.62 | 21.6 | 44.4 | 32.6 | 15.4 | 32.8 |
| 128 | Co-(treated)USY (Ex. 27) | 7.1 | 5.3 | 0.45 | 20.5 | 56.0 | 25.9 | 12.6 | 38.1 |
| 129 | Co-(treated)USY (Ex. 28) | 9.8 | 6.9 | 0.58 | 24.6 | 58.8 | 26.0 | 13.1 | 35.3 |
| 130 | Co-USY (s-s exch) (Ex. 29) | N/A | 3.0 | 0.23 | 24.1 | 58.1 | 26.8 | 7.6 | 32.3 |
| 131 | Co-ZSM-5 (Ex. 30) | N/A | 10.8 | 0.62 | 30.8 | 31.8 | 45.0 | 14.8 | 13.7 |

EXAMPLE 51

Effect of Dealumination Treatment

Tables 21–23 are further examples of this dramatic improvement in catalytic performance by dealumination treatment. The effect is illustrated over a few selected catalysts at different reaction temperatures. Dramatic increase of $C_2H_3N$ selectivity on treated Y catalysts can be seen at all three temperatures. The superior performance of these treated Y catalysts translates to lower raw material cost than previous catalysts.

TABLE 21

$C_2H_6$ Ammoxidation on Co-Y at 425° C. - Effect of Treatment

| Run | Catalyst | Conv. of $C_2H_6$ (%) | Selectivity based on $C_2H_6$ (%) | | | $C_2H_3N$ selec. based on $NH_3$ (%) | $C_2H_3N$ yield (%) |
|---|---|---|---|---|---|---|---|
| | | | $C_2H_3N$ | $C_2H_4$ | $CO_2$ | | |
| 132 | Co-Y (Ex. 22) | 6.2 | 39.8 | 28.9 | 30.1 | 18.2 | 2.5 |
| 133 | Co-Y (Ex. 23) | 6.2 | 40.6 | 18.4 | 31.6 | 27.9 | 2.5 |
| 134 | Co(treated)Y (Ex. 27) | 10.6 | 71.5 | 11.6 | 14.1 | 45.2 | 7.6 |
| 135 | Co(treated)Y (Ex. 28) | 11.2 | 68.5 | 15.3 | 14.2 | 37.1 | 7.7 |

TABLE 22

$C_2H_6$ Ammoxidation[a] on Co-Y at 450° C. - Effect of Treatment

| Run | Catalyst | Conv. of $C_2H_6$ (%) | Selectivity based on $C_2H_6$ (%) | | | $C_2H_3N$ selec. based on $NH_3$ (%) | $C_2H_3N$ yield (%) |
|---|---|---|---|---|---|---|---|
| | | | $C_2H_3N$ | $C_2H_4$ | $CO_2$ | | |
| 136 | Co-Y (Ex. 22) | 8.2 | 35.9 | 28.9 | 22.6 | 15.2 | 3.0 |
| 137 | Co-Y (Ex. 23) | 8.3 | 40.6 | 25.2 | 27.2 | 27.3 | 3.4 |
| 138 | Co(treated)Y (Ex. 27) | 14.6 | 59.2 | 17.6 | 17.7 | 39.2 | 8.6 |
| 139 | Co(treated)Y (Ex. 28) | 16.9 | 66.8 | 18.4 | 13.0 | 37.4 | 11.3 |

TABLE 23

$C_2H_6$ Ammoxidation[a] on Co-Y at 475° C. - Effect of Treatment

| Run | Catalyst | Conv. of $C_2H_6$ (%) | Selectivity based on $C_2H_6$ (%) | | | $C_2H_3N$ selec. based on $NH_3$ (%) | $C_2H_3N$ yield (%) |
|---|---|---|---|---|---|---|---|
| | | | $C_2H_3N$ | $C_2H_4$ | $CO_2$ | | |
| 140 | Co-Y (E. 22) | 12.2 | 27.9 | 45.7 | 18.2 | 13.4 | 3.4 |
| 141 | Co-Y (Ex. 23) | 12.7 | 36.1 | 38.7 | 20.0 | 23.9 | 4.6 |
| 142 | Co(treated)Y (Ex. 27) | 20.5 | 56.0 | 25.9 | 12.6 | 38.1 | 11.5 |
| 143 | Co(treated)Y (Ex. 28) | 24.6 | 58.8 | 26.0 | 13.1 | 35.3 | 14.5 |

The process of this invention offers a unique way to convert light alkanes and alkenes to value added chemicals. Acetonitrile, which is the principal nitrile product of process, can be hydrogenated to the amine. Currently organic amines are commonly made by amination of alcohols. This invention, therefore, provides a simple, direct route from refinery stocks to nitrogen derivatives, a process with industrial potential not heretofore available.

Other embodiments of our invention will be apparent to those skilled in the art the foregoing disclosure without departing from the spirit or scope of the invention.

We claim:

1. A process for producing acetonitrile which comprises contacting a feedstock comprising a source of hydrocarbon which is an alkane having from 2 to 6 carbon atoms, an alkene having from 2 to 6 carbon atoms or a mixture thereof, ammonia and oxygen with a catalyst comprising a base zeolite which has been exchanged with metal ions of Period 4, Groups VIIA and VIII of the Periodic Table at a temperature ranging from 300° to 600° C., a pressure ranging from atmospheric to 10 atmospheres, and a gas hourly space velocity ranging from 1000 to 100,000 volumes of feedstock per volume of catalyst per hour to form a product mixture consisting essentially of acetonitrile and recovering the acetonitrile.

2. The process of claim 1 wherein the hydrocarbon source is ethane, ethene or a mixture thereof.

3. The process of claim 1 wherein ammonia and the source of hydrocarbon are present in a molar ratio ranging from 0.1 to 10 and oxygen and the source of hydrocarbon are present in a molar ratio of from 0.1 to 10.

4. The process of claim 3 wherein the molar ratio of ammonia to the source of hydrocarbon ranges from 0.2 to 4 and the molar ratio of the oxygen to the source of hydrocarbon ranges from 0.5 to 2.

5. The process of claim 1 wherein the temperature ranges from 400° to 500° C. and the space velocity ranges from 5,000 to 20,000 volumes of feedstock per volume of catalyst per hour.

6. The process of claim 1 wherein the base zeolite is selected from the group consisting of ZSM-5, beta, NU-87, ZSM-11, mordenite, Y, chabazite and ferrierite.

7. The process of claim 6 wherein the metal ions are selected from the group consisting of divalent cobalt, divalent iron, trivalent iron, divalent nickel and divalent manganese.

8. The process of claim 6 wherein the metal ions are divalent cobalt.

9. The process of claim 1 wherein the catalyst comprises a base zeolite of ZSM-5 which has been exchanged with cobalt ions.

10. The process of claim 1 wherein the catalyst comprises a base zeolite of USY which has been exchanged with cobalt ions.

11. The process of claim 1 wherein the catalyst comprises a base zeolite of Beta which has been exchanged with cobalt ions.

12. The process of claim 1 wherein the catalyst comprises a base zeolite of ZSM-11 which has been exchanged with cobalt ions.

13. The process of claim 1 wherein the catalyst is impregnated with a boron-containing compound and calcined at a temperature ranging from 200° to 800° C. prior to conducting the process.

14. The process of claim 13 wherein the catalyst to be impregnated comprises a base zeolite of ZSM-5 which has been exchanged with cobalt ions.

15. The process of claim 13 wherein the catalyst to be impregnated comprises a base zeolite of Beta which has been exchanged with cobalt ions.

16. The process of claim 13 wherein the catalyst to be impregnated comprises a base zeolite of USY which has been exchanged with cobalt ions.

17. The process of claim 1 wherein the catalyst is impregnated with a phosphorous-containing compound and calcined at a temperature ranging from 200° to 800° C. prior to conducting the process.

18. The process of claim 17 wherein the catalyst to be impregnated comprises a base zeolite of ZSM-5 which has been exchanged with cobalt ions.

19. The process of claim 13 wherein the boron-containing compound is boric acid.

20. The process of claim 17 wherein the phosphorous-containing compound is ammonium hydrogen phosphate.

21. The process of claim 1 wherein the catalyst comprises a base zeolite of ZSM-5 which is silicon modified with an organic silicon compound and decomposed to silicon oxides prior to exchange with divalent cobalt ions.

22. The process of claim 1 wherein the base zeolite is Y which has a silicon to aluminum ratio of greater than 2.5.

23. The process of claim 1 wherein the base zeolite is exchanged with metal ions to yield a metal loading ranging from 1 to 10 weight percent.

24. The process of claim 1 wherein the product mixture comprises acetonitrile and alkene, wherein the alkene is separated from the product mixture and recycled into the process.

* * * * *